(12) United States Patent
Burkart et al.

(10) Patent No.: US 11,123,174 B2
(45) Date of Patent: Sep. 21, 2021

(54) EXTERNAL STEERABLE FIBER FOR USE IN ENDOLUMINAL DEPLOYMENT OF EXPANDABLE DEVICES

(71) Applicant: W. L. Gore & Associates, Inc., Newark, DE (US)

(72) Inventors: Dustin C. Burkart, Bellemont, AZ (US); Patrick M. Norris, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 161 days.

(21) Appl. No.: 15/691,299

(22) Filed: Aug. 30, 2017

(65) Prior Publication Data

US 2018/0036113 A1    Feb. 8, 2018

Related U.S. Application Data

(63) Continuation of application No. 14/084,428, filed on Nov. 19, 2013, now Pat. No. 9,770,322, which is a
(Continued)

(51) Int. Cl.
*A61F 2/07* (2013.01)
*A61F 2/97* (2013.01)
(Continued)

(52) U.S. Cl.
CPC .................. *A61F 2/07* (2013.01); *A61F 2/95* (2013.01); *A61F 2/958* (2013.01); *A61F 2/97* (2013.01);
(Continued)

(58) Field of Classification Search
CPC .. A61F 2/07; A61F 2/2439; A61F 2/95; A61F 2/958; A61F 2/962; A61F 2/966;
(Continued)

(56) References Cited

U.S. PATENT DOCUMENTS

| 1,355,373 A | 10/1920 | White |
| 1,506,432 A | 8/1924 | Kimmel |

(Continued)

FOREIGN PATENT DOCUMENTS

| CN | 101554343 | 10/2009 |
| CN | 101780306 | 7/2010 |

(Continued)

OTHER PUBLICATIONS

European Search Report for European Application No. 16155556.0 dated Aug. 1, 2016, 10 pages.
(Continued)

*Primary Examiner* — Wade Miles
*Assistant Examiner* — Kankindi Rwego

(57) ABSTRACT

The present disclosure describes treatment of the vasculature of a patient with an expandable implant. The implant is constrained to a reduced delivery diameter for delivery within the vasculature by at least one sleeve. The implant can be constrained to other diameters, such as an intermediate diameter. The sleeves can be expanded, allowing for expansion of the diameter of the expandable implant, by disengaging a coupling member from the sleeve or sleeves from outside of the body of the patient. The expandable implant can comprise a steering line or lines which facilitate bending and steering of the expandable implant through the vasculature of a patient.

16 Claims, 15 Drawing Sheets

Related U.S. Application Data continuation of application No. 13/743,118, filed on Jan. 16, 2013, now Pat. No. 9,375,308.

(60) Provisional application No. 61/610,372, filed on Mar. 13, 2012.

(51) Int. Cl.
*A61F 2/95* (2013.01)
*A61F 2/958* (2013.01)

(52) U.S. Cl.
CPC ..... *A61F 2/9517* (2020.05); *A61F 2002/9511* (2013.01); *A61F 2210/0076* (2013.01); *A61F 2250/0098* (2013.01)

(58) Field of Classification Search
CPC .. A61F 2/97; A61F 2002/9534; A61F 2/9517; A61F 2210/0076; A61F 2250/0098; A61F 2002/072; A61F 2002/075; A61F 2002/9505; A61F 2002/9511; A61F 2002/9522
USPC ........................................................ 623/1.12
See application file for complete search history.

(56) References Cited

U.S. PATENT DOCUMENTS

| | | | |
|---|---|---|---|
| 1,851,314 A | 3/1932 | Knoche |
| 3,625,451 A | 12/1971 | Anderson |
| 3,915,167 A | 10/1975 | Waterman |
| 3,953,566 A | 4/1976 | Gore |
| 4,187,390 A | 2/1980 | Gore |
| 4,503,569 A | 3/1985 | Dotter |
| 4,512,338 A | 4/1985 | Balko et al. |
| 4,655,246 A | 4/1987 | Philipot et al. |
| 4,858,810 A | 8/1989 | Intlekofer |
| 4,990,155 A | 2/1991 | Wilkoff |
| 5,037,427 A | 8/1991 | Harada et al. |
| 5,147,370 A | 9/1992 | McNamara et al. |
| 5,211,658 A | 5/1993 | Clouse |
| 5,217,486 A | 6/1993 | Rice et al. |
| 5,221,261 A | 6/1993 | Termin et al. |
| 5,276,276 A | 1/1994 | Gunn |
| 5,325,746 A | 7/1994 | Anderson |
| 5,344,427 A | 9/1994 | Cottenceau et al. |
| 5,491,704 A | 2/1996 | Duron |
| 5,527,338 A | 6/1996 | Purdy |
| 5,554,183 A | 9/1996 | Nazari |
| 5,562,726 A | 10/1996 | Chuter |
| 5,693,083 A | 12/1997 | Baker et al. |
| 5,707,376 A | 1/1998 | Kavteladze et al. |
| 5,709,704 A | 1/1998 | Nott et al. |
| 5,713,917 A | 2/1998 | Leonhardt et al. |
| 5,713,948 A | 2/1998 | Ulfacker |
| 5,720,776 A | 2/1998 | Chuter et al. |
| 5,725,552 A | 3/1998 | Kotula |
| 5,776,141 A | 7/1998 | Klein et al. |
| 5,776,186 A | 7/1998 | Uflacker |
| 5,782,909 A | 7/1998 | Quiachon et al. |
| 5,843,162 A | 12/1998 | Inoue |
| 5,873,906 A | 2/1999 | Lau et al. |
| 5,904,703 A | 5/1999 | Gilson |
| 5,961,546 A | 10/1999 | Robinson et al. |
| 6,013,093 A | 1/2000 | Nott et al. |
| 6,015,431 A | 1/2000 | Thornton et al. |
| 6,019,785 A | 2/2000 | Strecker |
| 6,042,588 A | 3/2000 | Munsinger et al. |
| 6,042,602 A | 3/2000 | Wells |
| 6,143,021 A | 11/2000 | Staeghle |
| 6,152,144 A | 11/2000 | Lesh |
| 6,165,195 A | 12/2000 | Wilson |
| 6,203,550 B1 | 3/2001 | Olson |
| 6,214,025 B1 | 4/2001 | Thistle et al. |
| 6,224,627 B1 | 5/2001 | Armstrong et al. |
| 6,231,561 B1 | 5/2001 | Frazier et al. |
| 6,231,581 B1 | 5/2001 | Shank et al. |
| 6,231,589 B1 | 5/2001 | Wessman et al. |
| 6,264,671 B1 | 7/2001 | Stack |
| 6,273,900 B1 | 8/2001 | Nott et al. |
| 6,312,454 B1 | 11/2001 | Stoeckel |
| 6,322,585 B1 | 11/2001 | Khosravi et al. |
| 6,328,727 B1 | 12/2001 | Frazier et al. |
| 6,346,117 B1 | 2/2002 | Greenhalgh |
| 6,352,561 B1 | 3/2002 | Leopold et al. |
| 6,451,051 B2 | 9/2002 | Drasler et al. |
| 6,475,234 B1 | 11/2002 | Richter |
| 6,485,513 B1 | 11/2002 | fan |
| 6,491,704 B2 | 12/2002 | Gifford, III et al. |
| 6,524,335 B1 | 2/2003 | Hartley et al. |
| 6,527,779 B1 | 3/2003 | Rourke |
| 6,551,303 B1 | 4/2003 | Van Tessel et al. |
| 6,551,350 B1 | 4/2003 | Thornton et al. |
| 6,572,643 B1 | 6/2003 | Gharibadeh |
| 6,572,646 B1 | 6/2003 | Boylan et al. |
| 6,689,150 B1 | 2/2004 | Van Tassel |
| 6,705,563 B2 | 3/2004 | Luo et al. |
| 6,712,836 B1 | 3/2004 | Berg et al. |
| 6,712,842 B1 | 3/2004 | Gifford, III et al. |
| 6,730,108 B2 | 5/2004 | Van Tassel |
| 6,733,521 B2 | 5/2004 | Chobotov et al. |
| 6,743,210 B2 | 6/2004 | Hart et al. |
| 6,746,472 B2 | 6/2004 | Frazier et al. |
| 6,755,854 B2 | 6/2004 | Gillick et al. |
| 6,827,731 B2 | 12/2004 | Armstrong et al. |
| 6,866,669 B2 | 3/2005 | Buzzard et al. |
| 6,884,259 B2 | 4/2005 | Tran et al. |
| 6,911,039 B2 | 6/2005 | Shiu |
| 6,926,732 B2 | 8/2005 | Derus et al. |
| 6,939,352 B2 | 9/2005 | Buzzard et al. |
| 6,945,990 B2 | 9/2005 | Greenan |
| 6,949,113 B2 | 9/2005 | Van Tassel |
| 6,974,471 B2 | 12/2005 | Van Schie |
| 6,994,092 B2 | 2/2006 | Van Der Burg et al. |
| 7,033,368 B2 | 4/2006 | Rourke |
| 7,044,134 B2 | 5/2006 | Khairkhahan |
| 7,049,380 B1 | 5/2006 | Chang et al. |
| 7,052,511 B2 | 5/2006 | Weldon et al. |
| 7,066,951 B2 | 6/2006 | Chovotov |
| 7,081,132 B2 | 7/2006 | Cook |
| 7,122,050 B2 | 10/2006 | Randall et al. |
| 7,128,073 B1 | 10/2006 | Van Der Burg et al. |
| 7,147,657 B2 | 12/2006 | Chiang et al. |
| 7,147,661 B2 | 12/2006 | Chobotov |
| 7,169,160 B1 | 1/2007 | Middleman et al. |
| 7,198,636 B2 | 4/2007 | Cully et al. |
| 7,208,003 B2 | 4/2007 | Davis et al. |
| 7,252,680 B2 | 8/2007 | Freitag |
| 7,331,992 B2 | 2/2008 | Randall et al. |
| 7,396,359 B1 | 7/2008 | DeRowe |
| 7,462,675 B2 | 12/2008 | Chang et al. |
| 7,555,034 B2 | 6/2009 | Shin et al. |
| 7,566,336 B2 | 7/2009 | Corcoran et al. |
| 7,572,289 B2 | 8/2009 | Sisken et al. |
| 7,601,159 B2 | 10/2009 | Ewers et al. |
| 7,611,528 B2 | 11/2009 | Goodson et al. |
| 7,655,034 B2 | 2/2010 | Mitchell et al. |
| 7,771,455 B2 | 8/2010 | Ken |
| 7,815,591 B2 | 10/2010 | Levine et al. |
| 7,837,724 B2 | 11/2010 | Keeble |
| 7,846,179 B2 | 12/2010 | Belef et al. |
| 7,887,580 B2 | 2/2011 | Randall et al. |
| 7,938,851 B2 | 5/2011 | Olson |
| 7,976,575 B2 | 7/2011 | Hartley |
| 7,998,189 B2 | 8/2011 | Kolbel et al. |
| 8,029,559 B2 | 10/2011 | Sisken et al. |
| 8,043,356 B2 | 10/2011 | Kolbel |
| 8,048,440 B2 | 11/2011 | Chang |
| 8,062,349 B2 | 11/2011 | Moore et al. |
| 8,080,032 B2 | 12/2011 | van der Burg |
| 8,167,927 B2 | 5/2012 | Chobotov |
| 8,231,650 B2 | 7/2012 | Cully |
| 8,241,346 B2 | 8/2012 | Chobotov |
| 8,241,350 B2 | 8/2012 | Randall et al. |

(56) References Cited

U.S. PATENT DOCUMENTS

| | | |
|---|---|---|
| 8,252,037 B2 | 8/2012 | Styrc et al. |
| 8,257,431 B2 | 9/2012 | Henderson |
| 8,262,671 B2 | 9/2012 | Osypka |
| 8,273,105 B2 | 9/2012 | Cohen et al. |
| 8,287,583 B2 | 10/2012 | LaDuca et al. |
| 8,328,861 B2 | 12/2012 | Martin |
| 8,361,135 B2 | 1/2013 | Dittman |
| 8,394,139 B2 | 3/2013 | Roeder |
| 8,424,166 B2 | 4/2013 | Dorneman et al. |
| 8,449,595 B2 | 5/2013 | Ouellette et al. |
| 8,469,990 B2 | 6/2013 | McGuckin |
| 8,480,725 B2 | 7/2013 | Rasmussen |
| 8,523,897 B2 | 9/2013 | van der Burg |
| 8,529,597 B2 | 9/2013 | Linder |
| 8,685,055 B2 | 4/2014 | Van Tassel |
| 8,690,911 B2 | 4/2014 | Miles |
| 8,834,519 B2 | 9/2014 | van der Burg |
| 8,870,947 B2 | 10/2014 | Shaw |
| 8,968,384 B2 | 3/2015 | Pearson |
| 8,979,919 B2 | 3/2015 | Goddard |
| 9,060,895 B2 | 6/2015 | Hartley |
| 9,095,466 B2 | 8/2015 | Norris |
| 9,132,025 B2 | 9/2015 | Aristizabal |
| 9,254,204 B2 | 2/2016 | Roeder |
| 9,265,596 B2 | 2/2016 | Shank |
| 9,308,349 B2 | 4/2016 | Rezac |
| 9,351,858 B2 | 5/2016 | Chobotov et al. |
| 9,375,308 B2 * | 6/2016 | Norris ................. A61F 2/95 |
| 9,498,361 B2 | 11/2016 | Roeder |
| 9,585,743 B2 | 3/2017 | Cartledge |
| 9,585,774 B2 | 3/2017 | Aristizabal |
| 9,681,968 B2 | 6/2017 | Goetz |
| 9,700,701 B2 | 7/2017 | Benjamin |
| 9,770,322 B2 * | 9/2017 | Burkart ................. A61F 2/95 |
| 9,782,282 B2 | 10/2017 | Bloss et al. |
| 9,782,284 B2 | 10/2017 | Hartley |
| 9,877,858 B2 | 1/2018 | Beard et al. |
| 9,937,070 B2 | 4/2018 | Skelton |
| 2001/0037142 A1 | 11/2001 | Stelter et al. |
| 2002/0007208 A1 | 1/2002 | Strecker et al. |
| 2002/0029077 A1 | 3/2002 | Leopold et al. |
| 2002/0091439 A1 | 7/2002 | Baker et al. |
| 2002/0099431 A1 | 7/2002 | Armstrong et al. |
| 2002/0151953 A1 * | 10/2002 | Chobotov ............... A61F 2/954 623/1.11 |
| 2003/0088305 A1 * | 5/2003 | Van Schie ............... A61F 2/06 623/1.12 |
| 2003/0098383 A1 | 5/2003 | Luo et al. |
| 2003/0149467 A1 | 8/2003 | Linder et al. |
| 2003/0181942 A1 | 9/2003 | Sutton |
| 2004/0034366 A1 | 2/2004 | Van der Burg et al. |
| 2004/0054396 A1 | 3/2004 | Hartley |
| 2004/0063805 A1 | 4/2004 | Pacetti et al. |
| 2004/0073289 A1 | 4/2004 | Hartley |
| 2004/0122503 A1 | 6/2004 | Campbell et al. |
| 2004/0138734 A1 | 7/2004 | Chobotov et al. |
| 2004/0143315 A1 | 7/2004 | Bruun et al. |
| 2005/0038470 A1 | 2/2005 | Van der Burg et al. |
| 2005/0049667 A1 | 3/2005 | Arbefeuille et al. |
| 2005/0070820 A1 | 3/2005 | Boutillette |
| 2005/0080476 A1 | 4/2005 | Gunderson et al. |
| 2005/0085890 A1 | 4/2005 | Rasmussen |
| 2005/0125031 A1 | 6/2005 | Pipenhagen et al. |
| 2005/0240257 A1 | 10/2005 | Ishimaru et al. |
| 2006/0004433 A1 | 1/2006 | Greenberg et al. |
| 2006/0015171 A1 | 1/2006 | Armstrong |
| 2006/0058833 A1 | 3/2006 | Vancamp |
| 2006/0155366 A1 | 7/2006 | LaDuca et al. |
| 2006/0198866 A1 | 9/2006 | Chang et al. |
| 2006/0254569 A1 | 11/2006 | Chipman |
| 2006/0264980 A1 | 11/2006 | Khairkhahan |
| 2007/0016281 A1 | 1/2007 | Melsheimer |
| 2007/0066993 A1 | 3/2007 | Kreidler |
| 2007/0088424 A1 | 4/2007 | Greenberg |
| 2007/0100427 A1 | 5/2007 | Perouse |
| 2007/0162048 A1 | 7/2007 | Quinn et al. |
| 2007/0167955 A1 | 7/2007 | Arnault de la Menardiere et al. |
| 2007/0198077 A1 | 8/2007 | Cully et al. |
| 2007/0198078 A1 | 8/2007 | Berra et al. |
| 2007/0219467 A1 | 9/2007 | Clark |
| 2007/0225797 A1 | 9/2007 | Krivoruhko |
| 2007/0248640 A1 | 10/2007 | Karabey |
| 2007/0249980 A1 | 10/2007 | Carrez et al. |
| 2007/0255390 A1 | 11/2007 | Ducke et al. |
| 2007/0270891 A1 | 11/2007 | McGuckin |
| 2008/0027529 A1 | 1/2008 | Hartley et al. |
| 2008/0178434 A1 | 1/2008 | Bulanda |
| 2008/0039925 A1 | 2/2008 | Ishimaru et al. |
| 2008/0114440 A1 | 5/2008 | Hlavka et al. |
| 2008/0147111 A1 | 6/2008 | Johnson |
| 2008/0208329 A1 | 8/2008 | Bishop |
| 2008/0269785 A1 | 10/2008 | Lampropoulos |
| 2008/0294234 A1 * | 11/2008 | Hartley ................. A61F 2/07 623/1.12 |
| 2009/0048656 A1 | 2/2009 | Wen |
| 2009/0054723 A1 | 2/2009 | Khairkhahan et al. |
| 2009/0062838 A1 | 3/2009 | Brumleve et al. |
| 2009/0082844 A1 | 3/2009 | Zacharias et al. |
| 2009/0099596 A1 | 4/2009 | McGuckin, Jr. |
| 2009/0099640 A1 | 4/2009 | Weng |
| 2009/0112249 A1 | 4/2009 | Miles |
| 2009/0171386 A1 | 7/2009 | Amplatz |
| 2009/0216308 A1 | 8/2009 | Hartley |
| 2009/0259291 A1 | 10/2009 | Kolbel et al. |
| 2010/0016943 A1 | 1/2010 | Chobotov |
| 2010/0023048 A1 | 1/2010 | Mach |
| 2010/0057195 A1 | 3/2010 | Roeder et al. |
| 2010/0094394 A1 | 4/2010 | Beach et al. |
| 2010/0094401 A1 | 4/2010 | Kolbel |
| 2010/0114290 A1 | 5/2010 | Rasmussen |
| 2010/0211052 A1 | 8/2010 | Brown et al. |
| 2010/0280591 A1 | 11/2010 | Shin |
| 2011/0040366 A1 | 2/2011 | Goetz et al. |
| 2011/0054515 A1 | 3/2011 | Bridgeman et al. |
| 2011/0054519 A1 | 3/2011 | Neuss |
| 2011/0066221 A1 | 3/2011 | White |
| 2011/0125252 A1 | 5/2011 | Goddard |
| 2011/0130821 A1 | 6/2011 | Styrc |
| 2011/0288624 A1 | 11/2011 | Roeder et al. |
| 2011/0313503 A1 | 12/2011 | Berra et al. |
| 2012/0022630 A1 | 1/2012 | Wubbeling |
| 2012/0022638 A1 | 1/2012 | Leewood et al. |
| 2012/0046652 A1 | 2/2012 | Sokel |
| 2012/0130473 A1 | 5/2012 | Norris et al. |
| 2012/0130474 A1 | 5/2012 | Buckley |
| 2012/0130475 A1 | 5/2012 | Shaw |
| 2012/0143305 A1 | 6/2012 | Berra et al. |
| 2012/0172965 A1 | 7/2012 | Kratzberg et al. |
| 2012/0172968 A1 | 7/2012 | Chuter et al. |
| 2012/0283773 A1 | 11/2012 | Van Tassel |
| 2012/0296360 A1 | 11/2012 | Norris et al. |
| 2012/0323270 A1 | 12/2012 | Lee |
| 2013/0023981 A1 | 1/2013 | Dierking et al. |
| 2013/0046371 A1 | 2/2013 | Greenberg et al. |
| 2013/0073029 A1 | 3/2013 | Shaw |
| 2013/0123896 A1 | 5/2013 | Bloss et al. |
| 2013/0138138 A1 | 5/2013 | Clark |
| 2013/0158647 A1 | 6/2013 | Norris |
| 2013/0178889 A1 | 7/2013 | Miles |
| 2013/0245666 A1 | 9/2013 | Larsen et al. |
| 2013/0245742 A1 | 9/2013 | Norris |
| 2013/0296912 A1 | 11/2013 | Ottma |
| 2014/0012303 A1 | 1/2014 | Heipl |
| 2014/0046360 A1 | 2/2014 | van der Burg |
| 2014/0277412 A1 | 9/2014 | Börtlein |
| 2014/0296908 A1 | 10/2014 | Ottma |
| 2014/0296909 A1 | 10/2014 | Heipl |
| 2014/0379019 A1 | 12/2014 | Larsen |
| 2015/0005809 A1 | 1/2015 | Ayres et al. |
| 2015/0005810 A1 | 1/2015 | Center |
| 2015/0051695 A1 | 2/2015 | Shaw |
| 2015/0305749 A1 | 10/2015 | Alferness |
| 2016/0331382 A1 | 11/2016 | Center |
| 2017/0056153 A1 | 3/2017 | Vinluan et al. |

(56) References Cited

U.S. PATENT DOCUMENTS

| | | | |
|---|---|---|---|
| 2017/0172724 A1 | 6/2017 | Cartledge | |
| 2017/0181751 A1 | 6/2017 | Larsen | |
| 2017/0281382 A1 | 10/2017 | Lostetter | |
| 2017/0367859 A1 | 12/2017 | Bloss et al. | |
| 2018/0071126 A1 | 3/2018 | Beard et al. | |
| 2019/0388256 A1 | 12/2019 | Chung et al. | |

FOREIGN PATENT DOCUMENTS

| | | | |
|---|---|---|---|
| CN | 103347467 A | 10/2013 | |
| EP | 0664107 A1 | 7/1995 | |
| EP | 0679372 | 11/1995 | |
| EP | 1474074 B1 | 4/2004 | |
| EP | 1441668 B1 | 1/2008 | |
| EP | 1915113 B1 | 3/2010 | |
| EP | 1358903 B1 | 2/2011 | |
| EP | 2481381 | 8/2012 | |
| EP | 2749251 B1 | 7/2016 | |
| EP | 3064173 A1 | 9/2016 | |
| EP | 2956198 B1 | 11/2017 | |
| EP | 3278771 A1 | 2/2018 | |
| FR | 2896405 | 7/2007 | |
| GB | 2344054 A | 5/2000 | |
| JP | 08-126704 A | 5/1996 | |
| JP | 1996126704 | 5/1996 | |
| JP | 2001-506902 A | 5/2001 | |
| JP | 2002-503114 A | 1/2002 | |
| JP | 2002-518086 A | 6/2002 | |
| JP | 2004167239 | 6/2004 | |
| JP | 2004-188219 A | 7/2004 | |
| JP | 2007-518465 A | 7/2007 | |
| JP | 2011-511693 A | 4/2011 | |
| JP | 2011-516202 A | 5/2011 | |
| JP | 2014-501563 A | 1/2014 | |
| JP | 2014-501565 A | 1/2014 | |
| JP | 2014-502180 A | 1/2014 | |
| JP | 2014-533189 A | 12/2014 | |
| WO | 96/18361 A1 | 6/1996 | |
| WO | WO-1997048350 A1 | 12/1997 | |
| WO | 98/27894 A1 | 7/1998 | |
| WO | 99/65420 A1 | 12/1999 | |
| WO | WO-2000013613 A1 | 3/2000 | |
| WO | WO-2001021109 A1 | 3/2001 | |
| WO | WO-2002028317 A2 | 4/2002 | |
| WO | 03/34948 A1 | 5/2003 | |
| WO | WO-03101518 A1 * | 12/2003 | ............... A61F 2/95 |
| WO | WO-2007092354 A2 | 8/2004 | |
| WO | WO-2008063464 A2 | 5/2005 | |
| WO | WO-2005072652 | 8/2005 | |
| WO | WO-2006007389 A1 | 1/2006 | |
| WO | 2008/047092 A1 | 4/2008 | |
| WO | WO-2009102441 A1 | 8/2009 | |
| WO | 2009/126227 A2 | 10/2009 | |
| WO | WO-2009148594 A1 | 12/2009 | |
| WO | WO-2010001012 A1 | 1/2010 | |
| WO | WO-2010090699 A1 | 1/2010 | |
| WO | WO-2010024881 | 3/2010 | |
| WO | WO-2010041038 A1 | 4/2010 | |
| WO | WO-2010044854 A1 | 4/2010 | |
| WO | WO-2010063795 A1 | 6/2010 | |
| WO | WO-2010081041 | 7/2010 | |
| WO | WO-2010105195 A2 | 9/2010 | |
| WO | WO-2011031981 | 3/2011 | |
| WO | WO-2011062858 A1 | 5/2011 | |
| WO | 2012/068257 A2 | 5/2012 | |
| WO | 2012/174254 A1 | 12/2012 | |
| WO | WO-2013040431 A1 | 3/2013 | |
| WO | 2013/074266 A1 | 5/2013 | |
| WO | WO-2013137977 A1 | 9/2013 | |
| WO | WO-2015132668 A1 | 9/2015 | |
| WO | 2018/165358 A1 | 9/2018 | |

OTHER PUBLICATIONS

European Search Report from EP17166472.5, dated Nov. 7, 2017, 7 pages.
Hsu et al, The Impact of Bird-Beak Configuration on Aortic Remodeling of Distal Arch Pathology After Thoracic Endovascular Aortic Repair with the Zenith Pro-Form TX2 Thoracic Endograft, Journal of Vascular Surgery, 2013, pp. 1-9.
International Preliminary Report on Patentability for PCT/US2012/055537, dated Mar. 18, 2014, 10 pages.
International Preliminary Report on Patentability for PCT/US2012055445 dated Mar. 18, 2014, 9 pages.
International Search Report & Written Opinion in International Application No. PCT/US/2012/055445, dated Dec. 5, 2012, 15 pages.
International Search Report and Written Opinion for PCT/US2012/055537, dated Dec. 5, 2012, 5 pages.
International Search Report and Written Opinion for PCT/US2012/061928 dated Jan. 22, 2013, corresponding to U.S. Appl. No. 13/658,597, 8 pages.
International Search Report and Written Opinion for PCT/US2013/022404 dated May 8, 2013, corresponding to U.S. Appl. No. 13/743,118, 7 pages.
International Search Report and Written Opinion from PCT/US2016/032487, dated Dec. 14, 2016, 20 pages.
Ueda et al, Incomplete Endograft Apposition to the Aortic Arch: Bird-Beak Configuration Increases Risk of Endoleak Formation after Thoracic Endovascular Aortic Repair, Radiology: vol. 255 No. 2; May 2010, pp. 645-652.
European Search Report and Search Opinion Received for EP Application No. 17190962.5, dated Nov. 20, 2017, 9 pages.
International Preliminary Report on Patentability received for PCT Patent Application No. PCT/US13/22404, dated Sep. 25, 2014, 11 pages.
International Preliminary Report on Patentability received for PCT Patent Application No. PCT/US14/66153, dated Jun. 2, 2016, 7 pages.
International Preliminary Report on Patentability received for PCT Patent Application No. PCT/US2012/061928, dated May 30, 2014, 7 pages.
International Search Report and Written Opinion for PCT/US2014/066153 dated Feb. 17, 2015, corresponding to U.S. Appl. No. 14/084,592, 5 pages.
International Search Report and Written Opinion received for PCT Patent Application No. PCT/US2012/061928, dated Jan. 22, 2013, 8 pages.
International Search Report PCT/US2013/022404 dated May 8, 2013, corresponding to U.S. Appl. No. 13/743,118.
Thread. (n.d) American Heritage (r) Dictionary of the English Language, Fifth Edition. (2011). Retrieved Feb. 14, 2016 from http://www.thefreedictionary.com/thread.
International Preliminary Report on Patentability received for PCT Patent Application No. PCT/US2018/021442, dated Sep. 19, 2019, 7 pages.
International Search Report and Written Opinion received for PCT Patent Application No. PCT/US2018/021442, dated Jul. 11, 2018, 8 pages.

* cited by examiner

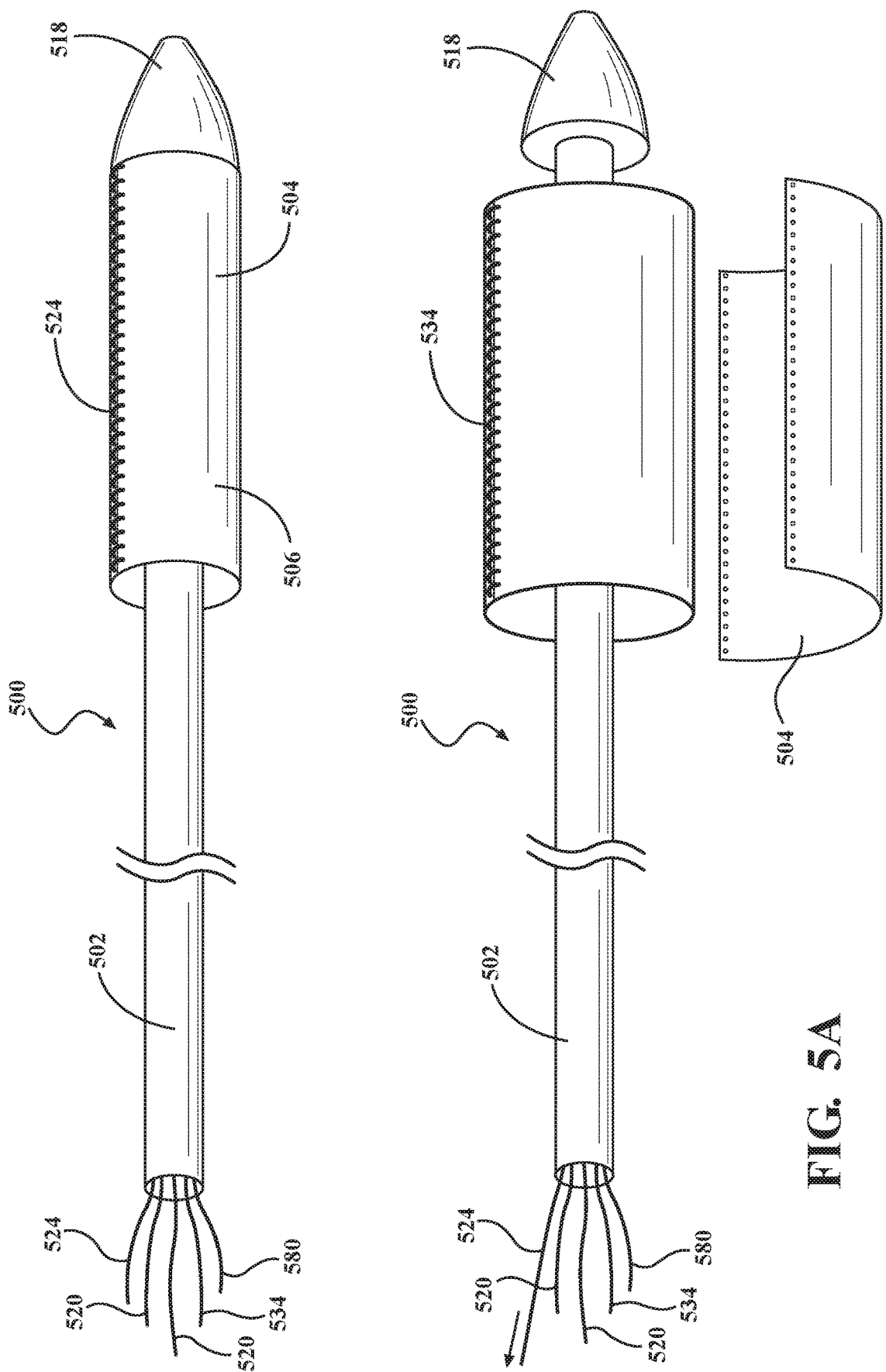

EXTERNAL STEERABLE FIBER FOR USE IN ENDOLUMINAL DEPLOYMENT OF EXPANDABLE DEVICES

CROSS-REFERENCE TO RELATED APPLICATIONS

This application is a CON of MP/407 (Ser. No. 13/743,118), filed Jan. 16, 2013, which claims priority to U.S. Provisional Application Ser. No. 61/610,372, entitled "EXTERNAL STEERABLE FIBER FOR USE IN ENDOLUMINAL DEPLOYMENT OF EXPANDABLE DEVICES" and filed Mar. 13, 2012, which is hereby incorporated by reference in its entirety.

BACKGROUND

Field

The present disclosure relates generally to endoluminal devices and, more specifically, to expandable endoluminal devices steerable within the vasculature of a patient.

Discussion of the Related Art

Endoluminal therapies typically involve the insertion of a delivery catheter to transport an implantable prosthetic device into the vasculature through a small, often percutaneous, access site in a remote vessel. Once access to the vasculature is achieved, the delivery catheter is used to mediate endoluminal delivery and subsequent deployment of the device via one of several techniques. In this fashion, the device can be remotely implanted to achieve a therapeutic outcome. In contrast to conventional surgical therapies, endoluminal treatments are distinguished by their "minimally invasive" nature.

Expandable endoluminal devices can be comprised of a graft or a stent component with or without a graft covering over the stent interstices. They can be designed to expand when a restraint is removed or to be balloon-expanded from their delivery diameter, through a range of intermediary diameters, up to a maximal, pre-determined functional diameter.

It remains desirable to provide improved systems for endoluminal delivery and deployment of expandable endoluminal devices to vascular treatment sites.

BRIEF DESCRIPTION OF THE DRAWINGS

The accompanying drawings are included to provide a further understanding of the disclosure and are incorporated in and constitute a part of this specification, illustrate embodiments of the disclosure and together with the description serve to explain the principles of the disclosure, wherein:

FIGS. 5A-5D illustrate perspective views of a catheter assembly having an expandable implant;

DETAILED DESCRIPTION

Figure 1:
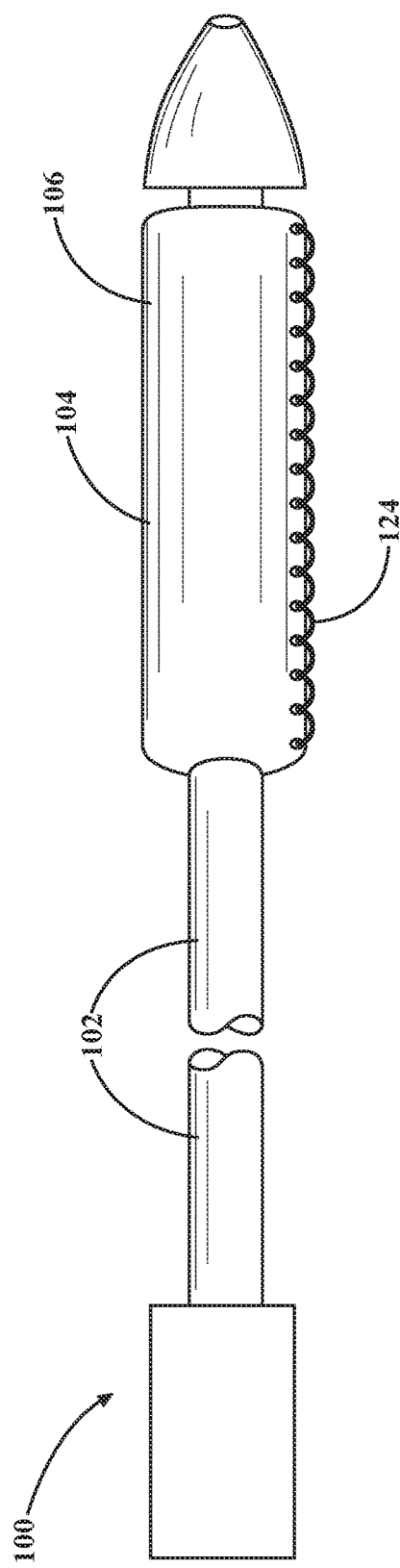
FIG. 1 illustrates a side view of a catheter assembly having an expandable implant.

Persons skilled in the art will readily appreciate that various aspects of the present disclosure can be realized by any number of methods and apparatuses configured to perform the intended functions. Stated differently, other methods and apparatuses can be incorporated herein to perform the intended functions. It should also be noted that the accompanying drawing figures referred to herein are not all drawn to scale, but can be exaggerated to illustrate various aspects of the present disclosure, and in that regard, the drawing figures should not be construed as limiting. Finally, although the present disclosure can be described in connection with various principles and beliefs, the present disclosure should not be bound by theory.

Throughout this specification and in the claims, the term "distal" refers to a location that is, or a portion of an endoluminal device (such as a stent-graft) that when implanted is, further downstream with respect to blood flow than another portion of the device. Similarly, the term "distally" refers to the direction of blood flow or further downstream in the direction of blood flow.

The term "proximal" refers to a location that is, or a portion of an endoluminal device that when implanted is, further upstream with respect to blood flow than another portion of the device. Similarly, the term "proximally" refers to the direction opposite to the direction of blood flow or upstream from the direction of blood flow.

With further regard to the terms proximal and distal, and because the present disclosure is not limited to peripheral and/or central approaches, this disclosure should not be narrowly construed with respect to these terms. Rather, the devices and methods described herein can be altered and/or adjusted relative to the anatomy of a patient.

Throughout this specification and in the claims, the term "leading" refers to a relative location on a device which is closer to the end of the device that is inserted into and progressed through the vasculature of a patient. The term "trailing" refers to a relative location on a device which is closer to the end of the device that is located outside of the vasculature of a patient.

In various embodiments, a catheter assembly is disclosed which utilizes one or more flexible sleeves that (i) releasably constrain an expandable implant, such as an expandable endoluminal stent graft, toward a dimension suitable for endoluminal delivery of the implant to a treatment site, such as a vascular member in a patient's body; and (ii) further constrain the implant to an outer peripheral dimension that is larger than the dimension suitable for endoluminal delivery but smaller than an unconstrained or fully deployed outer peripheral dimension, thereby facilitating selective axial and/or rotational positioning or other manipulation of the implant at the treatment site prior to full deployment and expansion of the implant.

Various embodiments of the present disclosure comprise a catheter assembly configured to deliver an expandable implant to a treatment area of the vasculature of a patient. In accordance with a number of embodiments, the catheter assembly includes at least one steering line that allows for selective bending of the expandable implant within the vasculature.

With initial reference to FIG. 1, a catheter assembly 100 in accordance with the present disclosure comprises an expandable implant 106. Expandable implant 106 can comprise any endoluminal device suitable for delivery to the treatment area of a vasculature. Such devices may include, for example, stents, grafts, and stent grafts. Thus, expandable implant can include one or more stent components with one or more graft members disposed over and/or under the stent, which can dilate from a delivery diameter, through a range of larger intermediary diameters, and toward a maximal, pre-determined functional diameter In various embodiments, expandable implant 106 comprises one or more stent components made of nitinol and a graft member made of ePTFE. However, and as discussed below, any suitable combination of stent component(s) and graft member(s) is within the scope of the present disclosure.

For example, stent components can have various configurations such as, for example, rings, cut tubes, wound wires (or ribbons) or flat patterned sheets rolled into a tubular form. Stent components can be formed from metallic, polymeric or natural materials and can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as stainless steels, cobalt-chromium alloys and nitinol and biologically derived materials such as bovine arteries/veins, pericardium and collagen. Stent components can also comprise bioresorbable materials such as poly(amino acids), poly(anhydrides), poly(caprolactones), poly(lactic/glycolic acid) polymers, poly(hydroxybutyrates) and poly(orthoesters). Any expandable stent component configuration which can be delivered by a catheter is in accordance with the present disclosure.

Moreover, potential materials for graft members include, for example, expanded polytetrafluoroethylene (ePTFE), polyester, polyurethane, fluoropolymers, such as perfouorelastomers and the like, polytetrafluoroethylene, silicones, urethanes, ultra high molecular weight polyethylene, aramid fibers, and combinations thereof. Other embodiments for a graft member material can include high strength polymer fibers such as ultra high molecular weight polyethylene fibers (e.g., Spectra®, Dyneema Purity®, etc.) or aramid fibers (e.g., Technora®, etc.). The graft member may include a bioactive agent. In one embodiment, an ePTFE graft includes a carbon component along a blood contacting surface thereof. Any graft member which can be delivered by a catheter is in accordance with the present disclosure.

In various embodiments, a stent component and/or graft member can comprise a therapeutic coating. In these embodiments, the interior and/or exterior of the stent component and/or graft member can be coated with, for example, a CD34 antigen. Additionally, any number of drugs or therapeutic agents can be used to coat the graft member, including, for example heparin, sirolimus, paclitaxel, everolimus, ABT-578, mycophenolic acid, tacrolimus, estradiol, oxygen free radical scavenger, biolimus A9, anti-CD34 antibodies, PDGF receptor blockers, MMP-1 receptor blockers, VEGF, G-CSF, HMG-CoA reductase inhibitors, stimulators of iNOS and eNOS, ACE inhibitors, ARBs, doxycycline, and thalidomide, among others.

In various embodiments, expandable implant 106 can comprise a radially collapsed configuration suitable for delivery to the treatment area of the vasculature of a patient. Expandable implant 106 can be constrained toward a radially collapsed configuration and releasably mounted onto a delivery device such as catheter shaft 102. The diameter of the expandable implant 106 in the collapsed configuration is small enough for the implant to be delivered through the vasculature to the treatment area. In various embodiments, the diameter of the collapsed configuration is small enough to minimize the crossing profile of catheter assembly 100 and reduce or prevent tissue damage to the patient. In the collapsed configuration, the expandable implant 106 can be guided by catheter shaft 102 through the vasculature.

In various embodiments, expandable implant 106 can comprise a radially expanded configuration suitable for implanting the device in the treatment area of a patient's vasculature. In the expanded configuration, the diameter of expandable implant 106 can be approximately the same as the vessel to be repaired. In other embodiments, the diameter of expandable implant 106 in the expanded configuration can be slightly larger than the vessel to be treated to provide a traction fit within the vessel.

In various embodiments, expandable implant 106 can comprise a self-expandable device, such as a self-expandable stent graft. Such devices dilate from a radially collapsed configuration to a radially expanded configuration when unrestrained. In other embodiments, expandable implant 106 can comprise a device that is expanded with the assistance of a secondary device such as, for example, a balloon. In yet other embodiments, catheter assembly 100 can comprise a plurality of expandable implants 106. The use of a catheter assembly with any number of expandable implants is within the scope of the present disclosure.

Various medical devices in accordance with the disclosure comprise a sleeve or multiple sleeves. The sleeve or sleeves may constrain an expandable implant device in a collapsed configuration for endoluminal delivery of the implant to a treatment portion of the vasculature of a patient. For the purposes of the disclosure, the term "constrain" may mean (i) to limit the expansion, either through self-expansion or assisted by a device, of the diameter of an expandable implant or (ii) to cover or surround but not otherwise restrain an expandable implant (e.g., for storage or biocompatibility reasons and/or to provide protection to the expandable implant and/or the vasculature). Catheter assembly 100, for example, comprises a sleeve 104 which surrounds and constrains expandable implant 106 toward a reduced diameter or collapsed configuration.

After deployment, the sleeve or sleeves can be removed in order to allow the expandable implant to expand toward a functional diameter and achieve a desired therapeutic outcome. Alternatively, the sleeve or sleeves can remain coupled to the implant or otherwise implanted while not interfering with the expandable implant.

In various embodiments, an expandable implant is constrained by a single sleeve which circumferentially surrounds the expandable implant. For example, with reference to FIG. 2B, catheter assembly 200 comprises a sleeve 204. In various embodiments, sleeve 204 circumferentially surrounds expandable implant 206 and constrains it toward a collapsed configuration, in which the diameter is less than the diameter of an unconstrained or otherwise deployed implant. For example, sleeve 204 may constrain expandable implant 206 toward a collapsed configuration for delivery within the vasculature.

In other embodiments, an expandable implant is constrained by a plurality of sleeves which circumferentially surround the expandable implant, which allow the expandable implant to be deployed and held at intermediate configurations larger than the collapsed configuration and smaller than the deployed configuration. The plurality of sleeves can comprise at least two sleeves which circumferentially surround each other.

In various embodiments, sleeves can be tubular and serve to constrain an expandable implant. In such configurations, sleeves are formed from a sheet of one or more materials wrapped or folded about the expandable implant. While the illustrative embodiments herein are described as comprising one or more tubular sleeves, sleeves of any non-tubular shape that corresponds to an underlying expandable implant or that are otherwise appropriately shaped for a given application are also within the scope of the present disclosure.

In various embodiments, sleeves are formed by wrapping or folding the sheet of material(s) such that two parallel edges of the sheet are substantially aligned. Said alignment may or may not be parallel to or coaxial with the catheter shaft of a catheter assembly. In various embodiments, the edges of the sheet of material(s) do not contact each other.

In various embodiments, the edges of the sheet of material(s) do contact each other and are coupled with a coupling member (as described below) an adhesive, or the like. In various other embodiments, the edges of the sheet of material(s) are aligned so that the edges of the same side of the sheet or sheets (e.g., the front or back of the sheet) are in contact with each other. In still other embodiments, the edges of opposite sides of the sheet of material(s) are in contact with each other, such that the edges overlap each other, such that a portion of one side of the sheet is in contact with a portion of the other side. Said another way, the front of the sheet may overlap the rear of the sheet, or vice versa.

In various embodiments, sleeves comprise materials similar to those used to form a graft member. For example, a precursor flexible sheet used to make the sleeve can be formed from a flattened, thin wall ePTFE tube. The thin wall tube can incorporate "rip-stops" in the form of longitudinal high strength fibers attached or embedded into the sheet or tube wall.

The sheet of material(s) used to form the sleeve(s) can comprise a series of openings, such that the openings extend from one edge of the sheet to the other. In such configurations, a coupling member can be woven or stitched through the series of openings in the sheet of material(s), securing each of the two edges together and forming a tube. For example, in FIG. 1, coupling member 124 secures the edges of sleeve 104 such that sleeve 104 maintains expandable implant 106 toward a reduced diameter or outer peripheral dimension suitable for endoluminal delivery.

In various embodiments, the coupling member can comprise a woven fiber. In other embodiments, the coupling member can comprise a monofilament fiber. Any type of string, cord, thread, fiber, or wire which is capable of maintaining a sleeve in a tubular shape is within the scope of the present disclosure.

In various embodiments, a single coupling member can be used to constrain the diameter of one or more sleeves. In other embodiments, multiple coupling members can be used to constrain the diameter of one or more sleeves.

Once a suitable expandable implant is in a collapsed configuration, the expandable implant can be deployed within the vasculature of a patient. An expandable implant in a collapsed configuration can be introduced to a vasculature and directed by a catheter assembly to a treatment area of the vasculature. Once in position in the treatment area of the vasculature, the expandable implant can be expanded to an expanded configuration.

When the expandable implant is in position within the vasculature, the coupling member or members can be disengaged from the sleeve or sleeves from outside of the body of the patient, which allows the sleeve(s) to open and the expandable implant to expand. As discussed above, the expandable implant can be self-expanding, or the implant can be expanded by an expanding device, such as a balloon.

The coupling member or members can be disengaged from the sleeve or sleeves by a mechanical mechanism operated from outside of the body of the patient. For example, the member or members can be disengaged by applying sufficient tension to the member or members. In another example, a translatable element can be attached to the coupling member or members outside of the body. Displacement of the translatable elements, such as rotation of a dial or rotational member or translation of a handle or knob, may provide sufficient tension to displace and disengage the coupling member or members.

In various embodiments, disengaging a single coupling member which closes a single sleeve from the sleeve allows the expandable device to be expanded toward a larger diameter or outer peripheral dimension. For example, with reference to FIG. 2A, catheter assembly 200 can be used to deliver an implant expandable implant 206 to a treatment area of a vasculature. Expandable implant 206 has a collapsed diameter for delivery, and sleeve 204 circumferentially surrounds expandable implant 206 and is held closed by coupling member 224. As described in more detail below, bending of expandable implant 206 can be controlled prior to full expansion (e.g., at an intermediate diameter) to help facilitate delivery to the desired position. Once expandable implant 206 is in position relative to the treatment area, coupling member 224 is disengaged from sleeve 204 and sleeve 204 is released, allowing expandable implant 206 to expand toward a larger diameter.

As mentioned above, in various embodiments of the present disclosure, an expandable implant may further comprise an intermediate configuration. In the intermediate configuration, the diameter of the expandable implant is constrained in a diameter smaller than the expanded configuration and larger than the collapsed configuration. For example, the diameter of the expandable device in the intermediate configuration can be about 50% of the diameter of the expandable device in the expanded configuration. However, any diameter of the intermediate configuration which is less than the diameter of the expanded configuration and larger than the collapsed configuration is within the scope of the invention.

In such embodiments, the expandable implant can be expanded from the collapsed configuration toward the intermediate configuration once the implant has been delivered near the treatment area of the vasculature of a patient. The intermediate configuration may, among other things, assist in properly orienting and locating the expandable implant within the treatment area of the vasculature.

In various embodiments, an expandable implant can be concentrically surrounded by two sleeves having different diameters. In such configurations, a primary sleeve constrains the expandable implant toward the collapsed configuration. Once the collapsed configuration sleeve is opened, a secondary sleeve constrains the expandable implant toward the intermediate configuration. As discussed above, the expandable implant can be self-expanding, or the implant can be expanded by a device, such as a balloon.

Figure 2A:
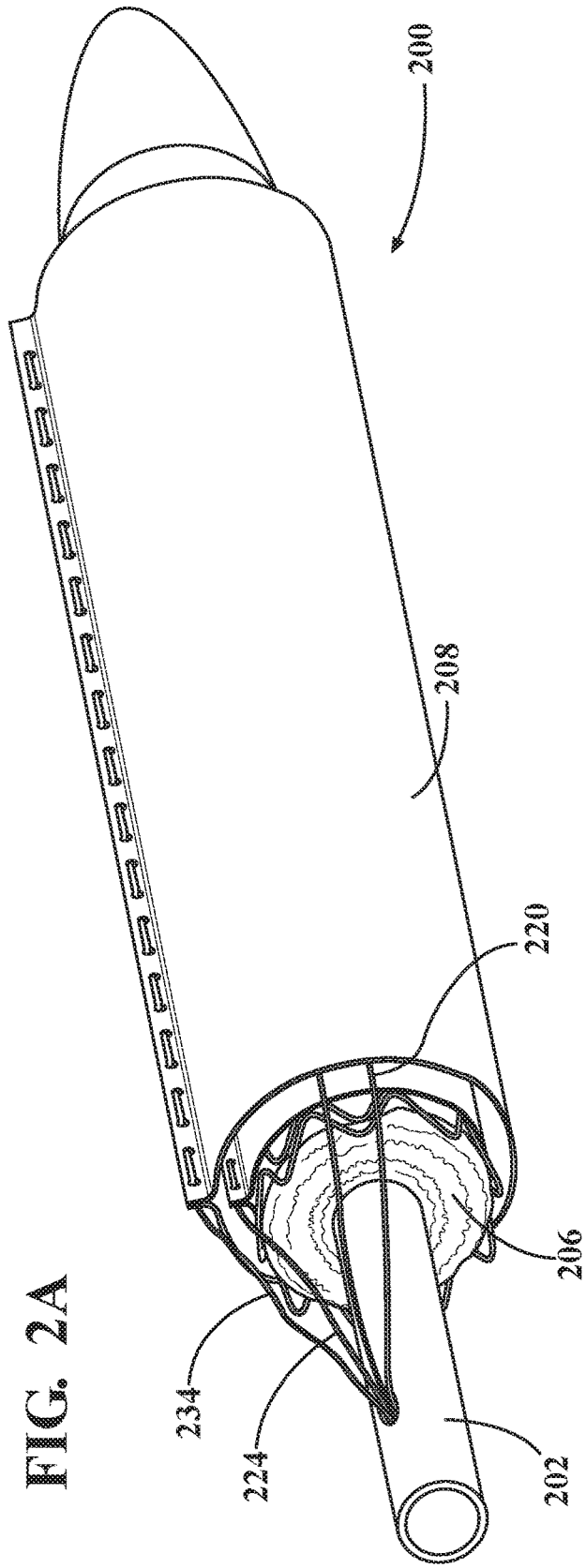
FIGS. 2A and 2B illustrate perspective views of catheter assemblies having expandable implants.

For example, with reference to FIG. 2A, a catheter assembly 200 comprises an expandable implant 206 and sleeve 204. Secondary sleeve 204 constrains expandable implant 206 toward an intermediate configuration. Secondary sleeve 204 is held in position around expandable implant 206 by secondary coupling member 224.

Catheter assembly 200 further comprises a primary sleeve 208, which constrains expandable implant 206 toward a collapsed configuration for delivery to the vasculature of a patient. Primary sleeve 208 is held in position around expandable implant 206 by primary coupling member 234.

Once expandable implant 206 is sufficiently close to the treatment area of the vasculature, primary coupling member 234 is disengaged from primary sleeve 208, which releases primary sleeve 208 and allows expanded implant 206 to expand toward a larger diameter.

Figure 2B:
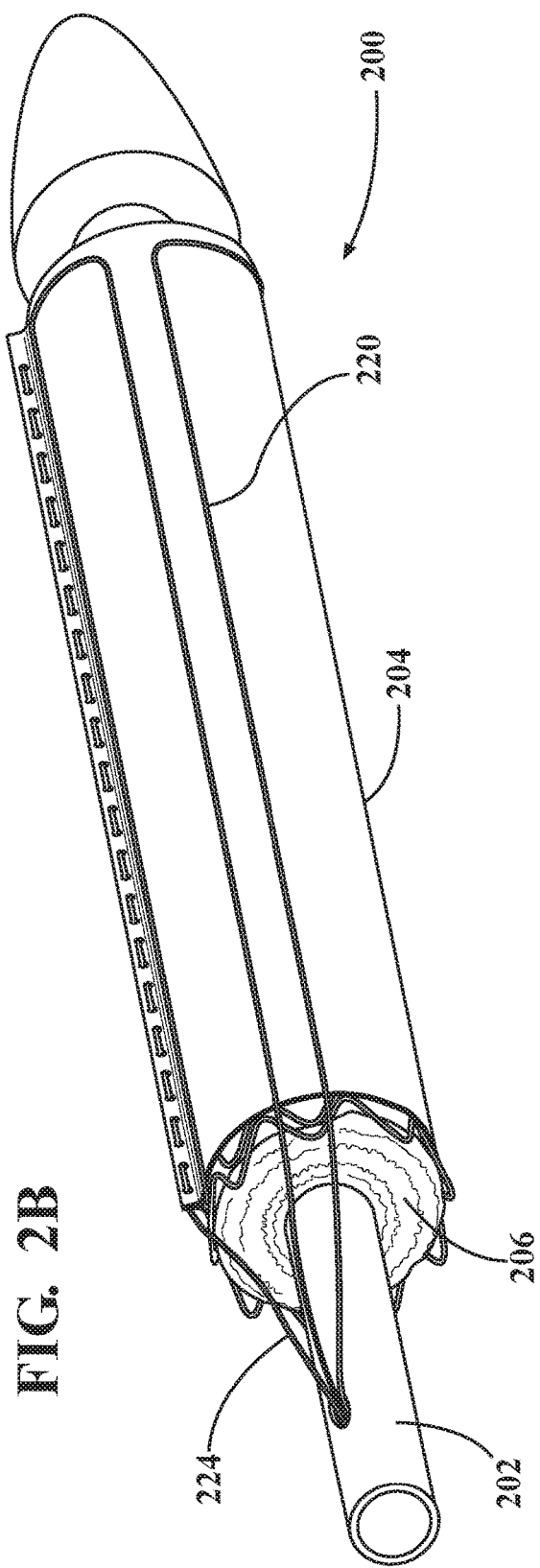

With reference to FIG. 2B, after primary sleeve 208 has been expanded, secondary sleeve 204 constrains the expandable implant 206 toward the intermediate configuration. In the intermediate configuration, as mentioned above and as described in more detail below, expandable implant 206 can be oriented and adjusted (e.g., by bending and torsional rotation) to a desired location within the treatment area of the vasculature.

In other embodiments of the present disclosure, a single or "mono" sleeve can be used to constrain the expandable implant in both a collapsed configuration and an intermediate configuration. For example, with reference to FIGS. 3A-3D, catheter assembly 300 comprises an expandable implant 306, a monosleeve 304, a primary coupling member 334, and a secondary coupling member 324.

Monosleeve 304 further comprises a plurality of secondary holes 332. In this configuration, secondary coupling member 324 is stitched or woven through secondary holes 332, constricting monosleeve 304 and expandable implant 306 to the diameter of an intermediate configuration. In the intermediate configuration, the diameter of expandable implant 306 is less than the expanded diameter and larger than the diameter of the collapsed configuration. In the intermediate configuration, as described in more detail below, expandable implant 306 can be oriented and adjusted (e.g., by bending and torsional rotation) to a desired location within the treatment area of the vasculature.

Monosleeve 304 further comprises a plurality of primary holes 330. In this configuration, primary coupling member 334 is stitched or woven through primary holes 330, constricting monosleeve 304 and expandable implant 306 toward the collapsed configuration. The diameter or outer peripheral dimension of the collapsed configuration is selected to allow for endoluminal delivery of the expandable implant 306 to the treatment area of the vasculature of a patient.

Once expandable implant 306 has been delivered to a region near the treatment area of the vasculature, primary coupling member 334 can be disengaged from monosleeve 304, allowing expandable implant 306 to be expanded toward the intermediate configuration. Expandable implant 306 can be oriented and adjusted (e.g., by bending and torsionally rotating) to a desired location within the treatment area of the vasculature. After final positioning, secondary coupling member 324 can be disengaged from monosleeve 304, and expandable implant 306 can be expanded toward the expanded configuration.

Although a number of specific configurations of constraining members (for example, primary and secondary members) and sleeves (for example, primary and secondary sleeves) have been discussed, the use of any number and/or configuration of constraining members and any number of sleeves is within the scope of the present disclosure. Further, the expandable implant may be allowed to partially expand toward the intermediate and expanded configurations by partially selectively disengaging the secondary and primary coupling members from the monosleeve, respectively.

In various embodiments, the catheter assembly further comprises a steering line. In such configurations, tension can be applied to the steering line to displace the steering line and bend the expandable implant. Bending the expandable implant may, among other things, assist in travelling through curved or tortuous regions of vasculature. Bending the expandable implant may also allow the implant to conform to curvatures in the vasculature of a patient.

For example, with reference to FIGS. 2A-2B, steering line 220 passes from the outside of the body of a patient, through catheter shaft 202, and is releasably coupled to expandable implant 206. In such configurations, steering line 220 can be threaded through expandable implant 206 such that tension applied to steering line 220 from outside of the body of the patient causes expandable implant 206 to bend in a desired manner.

Figure 6:
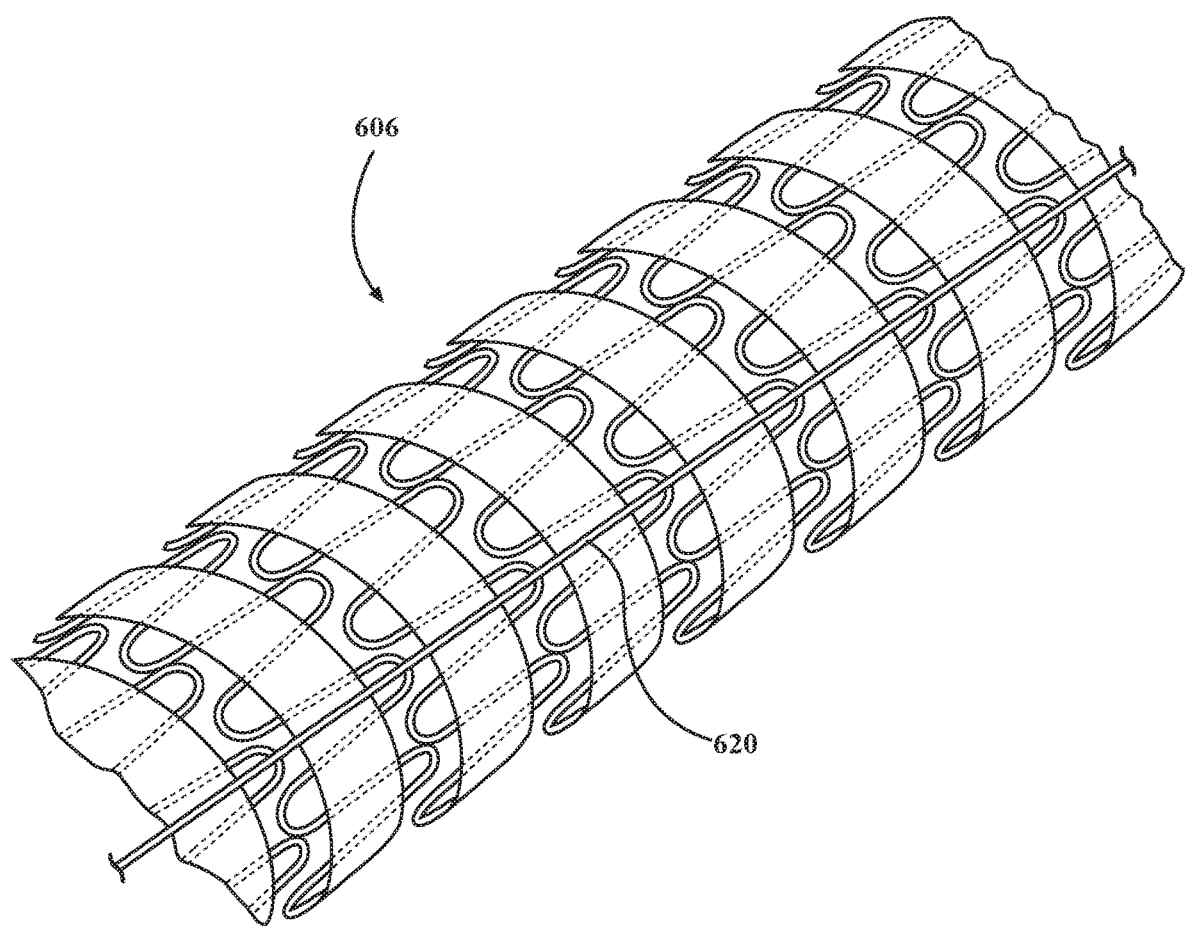
FIG. 6 illustrates a perspective view of an expandable implant.

As a further example, with reference to FIG. 6, an expandable implant 606 is illustrated. Steering line 620 is threaded along the surface of expandable implant 606.

In various embodiments, steering line 220 can comprise metallic, polymeric or natural materials and can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as stainless steels, cobalt-chromium alloys and nitinol. Elongated members or lock wires can also be formed from high strength polymer fibers such as ultra high molecular weight polyethylene fibers (e.g., Spectra®, Dyneema Purity®, etc.) or aramid fibers (e.g., Technora®, etc.).

With reference to FIGS. 7A-H, cross-sectional views of various expandable implant configurations are illustrated. In various embodiments, an expandable implant can comprise a stent 705 and a graft member 707, which are surrounded by sleeve 704. In such configurations, a steering line 720 can be threaded through stent 705, graft member 707, and/or sleeve 704 in a variety of different patterns. Such patterns may, among other benefits, facilitate the bending of the expandable implant by applying tension to (and corresponding displacement of) steering line 720 from outside of the body. Further, such patterns may reduce or prevent steering line 720 from damaging tissue within the vasculature of the patient by limiting or preventing "bowstringing." Bowstringing occurs when a string or thread travels in a direct line between two points on the inside of a curve in an expandable graft. This may cause the string or thread to come into contact with and potentially damage tissue in the vasculature. Bowstringing and its effects on tissue may also be reduced and/or minimized by sleeve 704 as sleeve 704 surrounds steering line 720 during bending and prior to full expansion of the expandable implant.

As illustrated in FIGS. 7B-7H, steering line 720 can be woven through any combination of stent 705, graft member 707, and sleeve 704. In each figure described below, a segment of a pattern is described. A steering line can be woven between a stent, graft member, and sleeve in any combination of these patterns. Alternatively, the steering line may interact with an expandable implant and one or more sleeves in any manner which allows steering line 720 to bend the expandable implant in a desired manner.

Figure 7A:
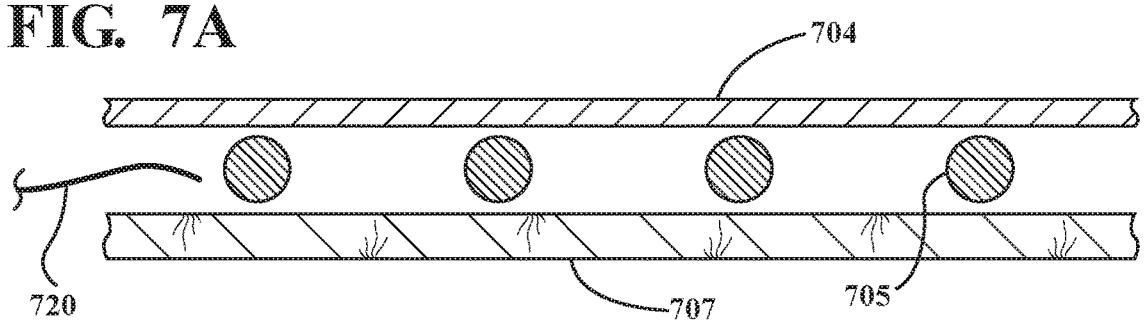
FIGS. 7A-7H illustrate cross-sectional views of an expandable implant and sleeve.
Figure 7B:
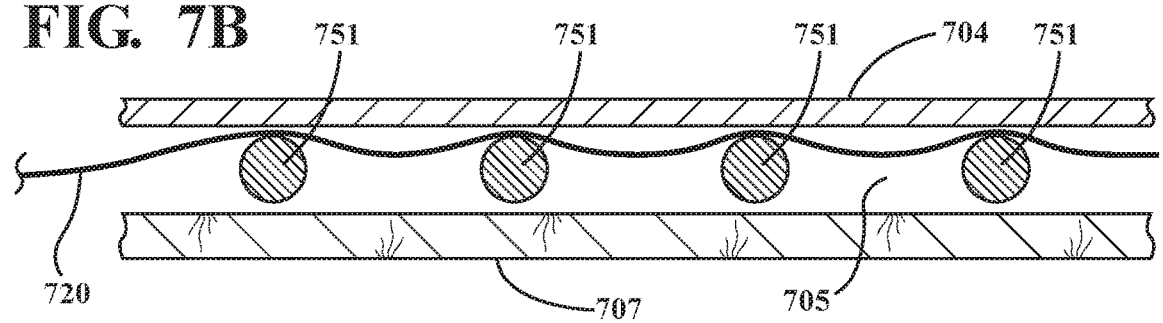
Figure 7C:
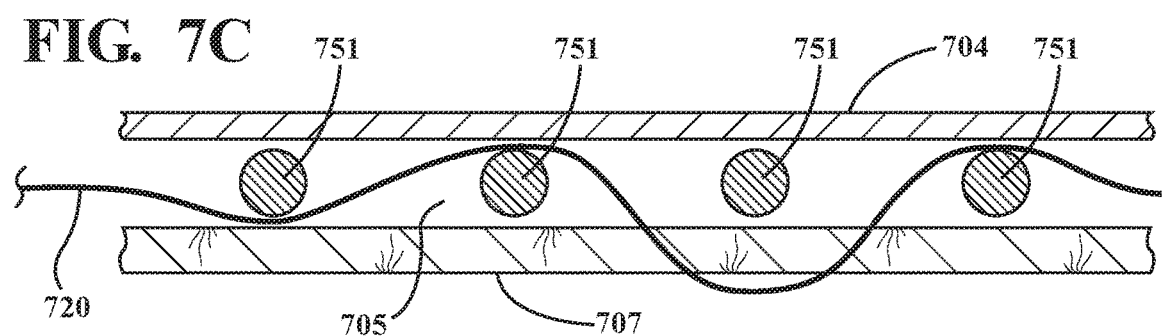
Figure 7D:
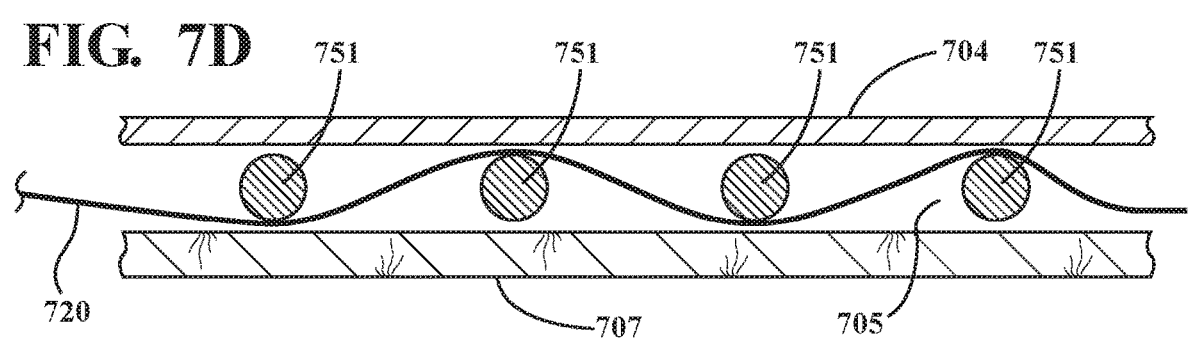

In FIG. 7B, steering line 720 is threaded between the inner wall of sleeve 704 and stent 705. In FIG. 7C, steering line 720 passes between a first apex 751 of stent 705 and the outer wall of graft member 707, passes between second apex 742 and the inner wall of sleeve 704, extends into and through the wall of graft member 707, reenters graft member 707, passes between a third apex 753 of stent 705 and the inner wall of sleeve 704, and passes between a fourth apex 754 and the inner wall of sleeve 704. In FIG. 7D, steering line 720 passes between first apex 751 and the outer wall of graft member 707, then between second apex 752 and the inner wall of sleeve 704.

Figure 7E:
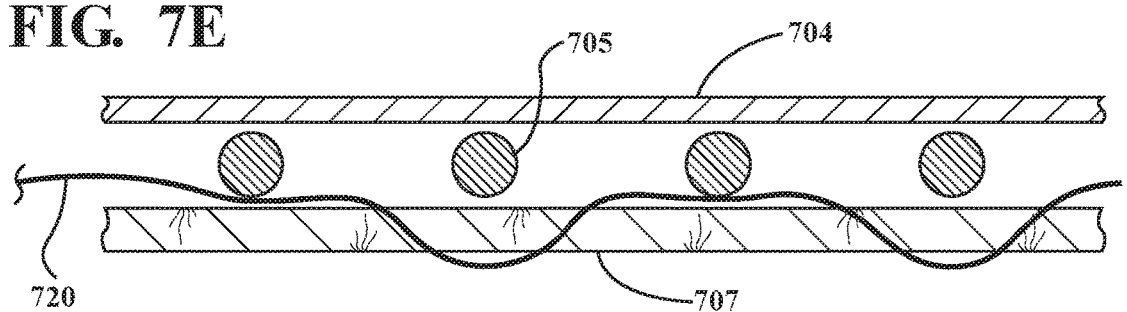
Figure 7F:
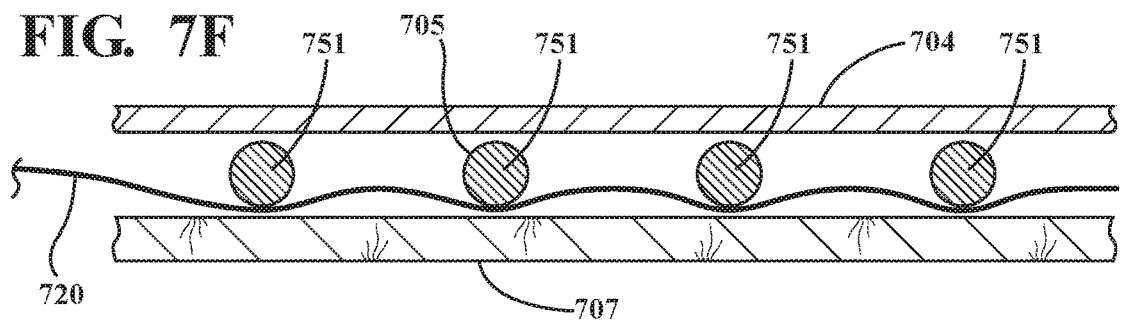

In FIG. 7E, steering line 720 passes between first apex 751 and the outer wall of graft member 707, extends through the outer wall of graft member 707, reenters graft member 707, and passes between third apex 753 and the outer wall of graft member 707 In FIG. 7F, steering line 720 passes between the outside wall of graft member 707 and stent 705.

Figure 7G:
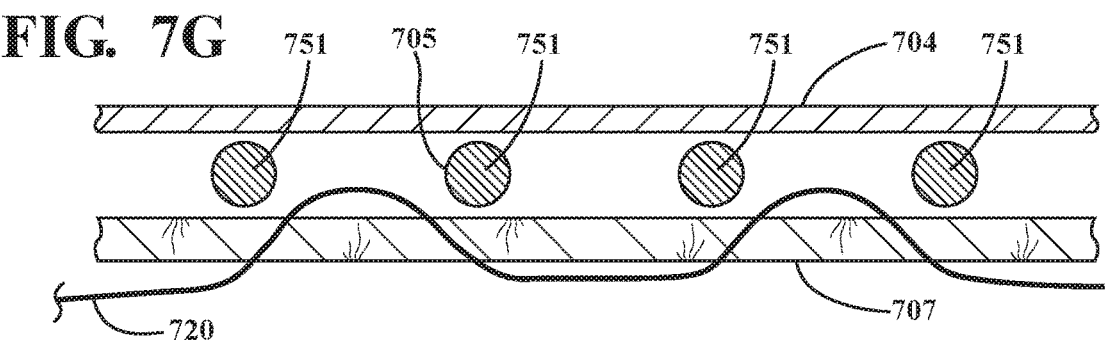
Figure 7H:
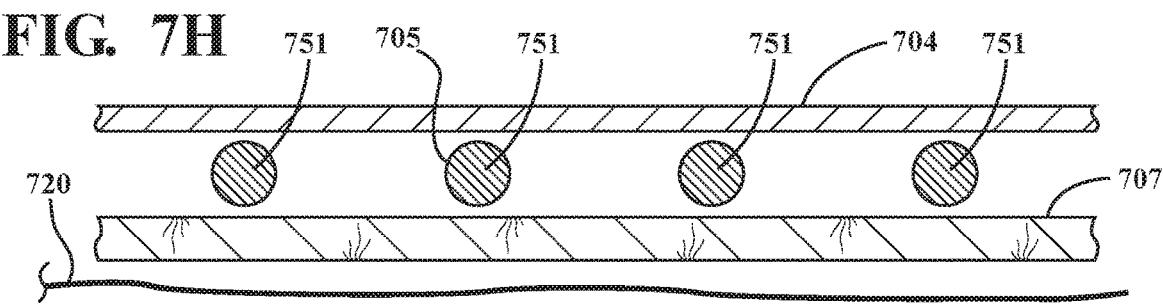

In FIG. 7G, steering line 720 passes from the inner wall of graft member 707, through to the outer wall of graft member 707 between first apex 751 and second apex 752, back through to the outer wall of graft member 707, and back through to the inner wall of graft member 707 between third apex 753 and fourth apex 754. In FIG. 7H, steering line 720 is disposed against the inner wall of graft member 707. As discussed previously, FIGS. 7B-7G illustrate example patterns in which a steering line may interact with an expandable implant. Any way in which a steering line interacts with an expandable implant to facilitate bending of the implant is within the scope of the present disclosure.

In various embodiments, a catheter assembly can comprise more than one steering line. For example, with reference to FIG. 9, catheter assembly 900 comprises two steering lines 920. As described in relation to FIGS. 7A-7G, steering lines 920 can be woven through the surface of expandable implant 906. In various embodiments, steering lines 920 may exit catheter shaft 902 and engage expandable implant 906 near the proximal end of expandable implant 906. In such configurations, steering lines 920 may travel across and remain substantially in contact with the surface of expandable implant 906 from the proximal end to the distal end. Steering line 920 may then disengage the surface of expandable implant 906 and become secured to catheter assembly 900.

Figure 9:
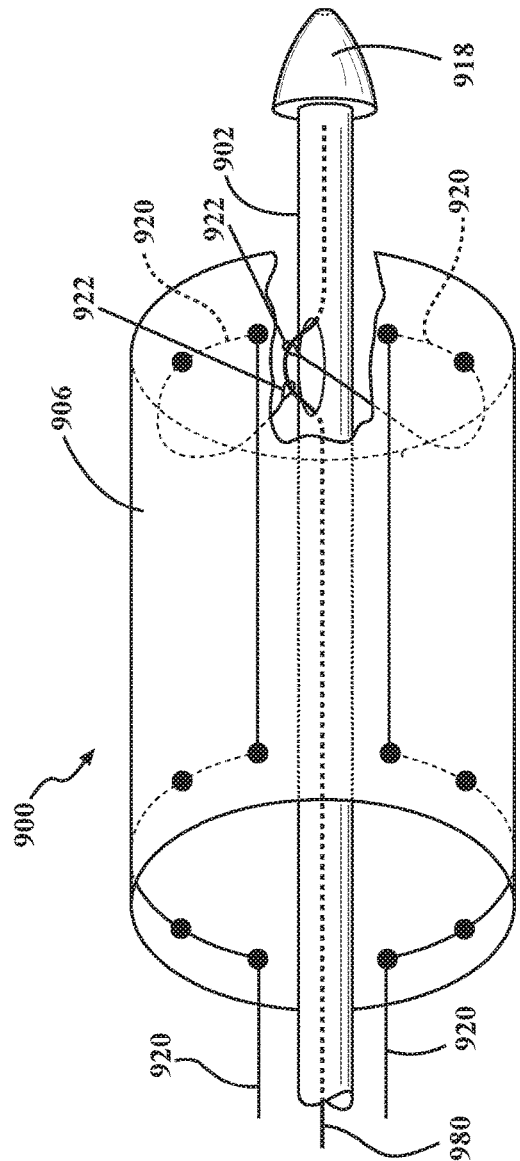
FIG. 9 illustrates a side view of a catheter assembly having an expandable implant.

In various embodiments, steering lines 920 traverse and interact with the surface of expandable implant 906 in a pattern which facilitates controllable bending of expandable implant 906. For example, as illustrated in FIG. 9, steering lines 920 may traverse the surface of expandable implant 906 such that, across a significant portion of expandable implant 906, both steering lines 920 are parallel to and in close proximity with each other. Such a configuration allows the tension applied to steering lines 920 to work together to form a bend or curvature in the same segment of expandable implant 906. Any configuration of steering lines 920 and surface of expandable implant 906 which allows for selective and controllable bending of expandable implant 906 is within the scope of the present disclosure.

In various embodiments, one or more steering lines are configured to enable selective and controllable bending of an expandable implant, for example as described above, and also to enable non-concentric, temporary engagement of an expandable implant in relation to a catheter assembly. For example, it can be desirable for a portion of the inner surface of an expandable implant to be temporarily engaged distal to a catheter assembly. Such a portion, for example, can be that which will exhibit the longest radius of curvature during selective and controllable bending of the expandable implant, whether during and/or after its delivery and deployment. Such a portion can thus be an outer curve portion of an expandable implant.

To accomplish the aforesaid objectives, in various embodiments, one or more steering lines can begin and terminate at distal and proximal ends respectively along an edge of an expandable implant which will exhibit the longest radius of curvature during selective and controllable bending. Between the distal and proximal ends, the one or more steering lines can transition toward and along an edge of an expandable implant which will exhibit the shortest radius of curvature during selective and controllable bending.

Figure 10A:
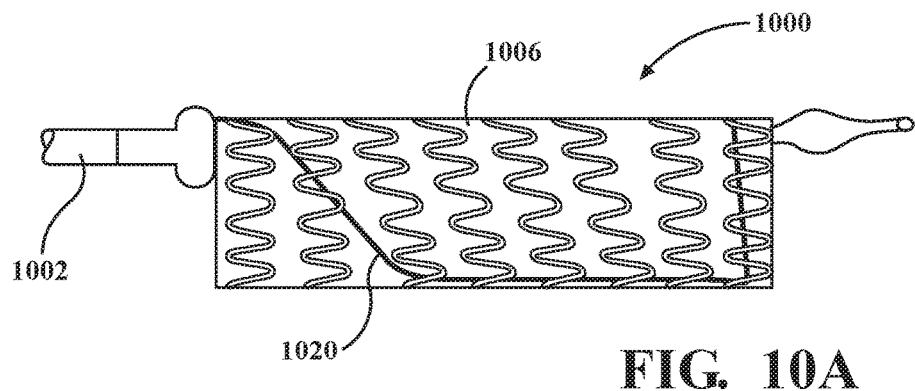
FIG. 10A illustrates a side view of a catheter assembly having an expandable implant.

For example, with reference to FIG. 10A, a catheter assembly 1000 is illustrated as having a catheter shaft 1002 temporarily engaged distal to an outer curve portion of the inner surface of an expandable implant 1006 by two steering lines 1020, each comprising a helical pattern. As described in relation to FIGS. 7A-7G, steering lines 1020 can be woven through the surface of expandable implant 1006. In various embodiments, steering lines 1020 may exit catheter shaft 1002 and engage expandable implant 1006 near the distal end of expandable implant 1006. In such configurations, steering lines 1020 may travel across and remain substantially in contact with the surface of expandable implant 1006 from the distal end to the proximal end. Steering line 1020 may then disengage the surface of expandable implant 1006 and become secured to catheter assembly 1000.

Figure 10B:
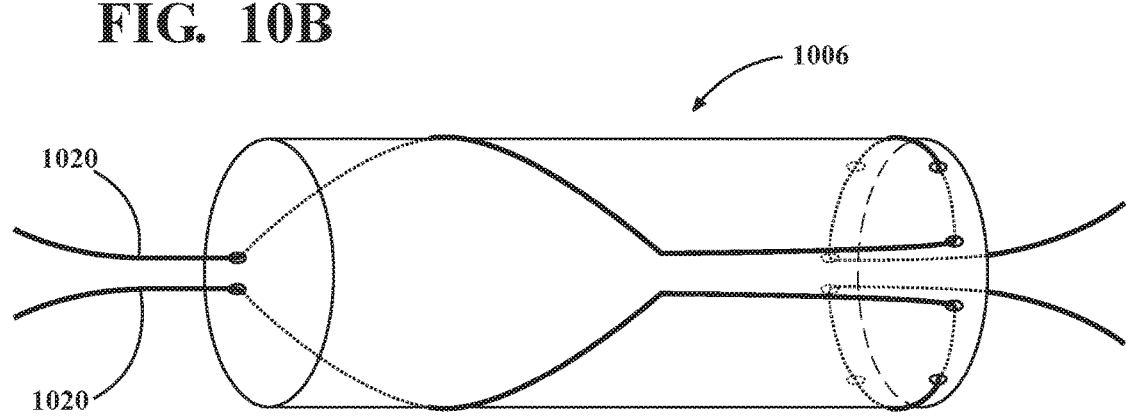
FIGS. 10B-10D illustrate inner curve, outer curve, and open views respectively of the expandable implant and steering lines illustrated in FIG. 10A.
Figure 10C:
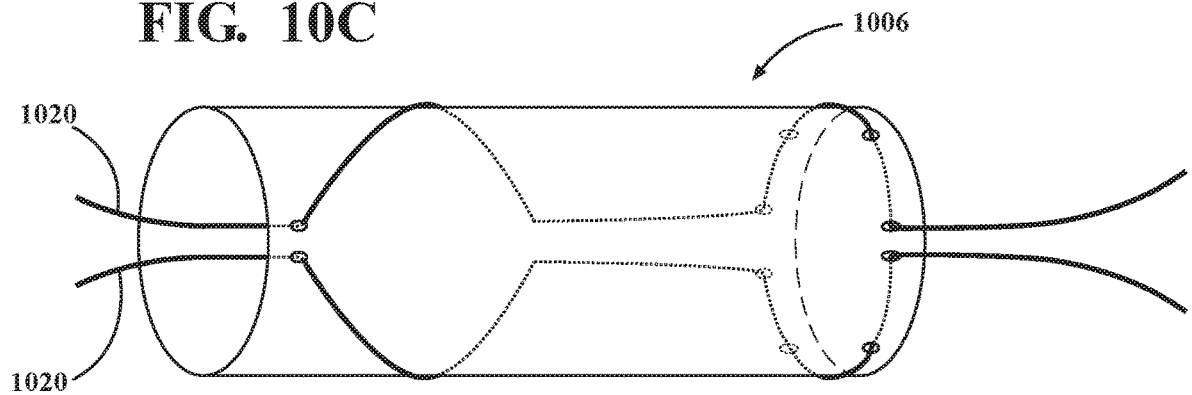
Figure 10D:
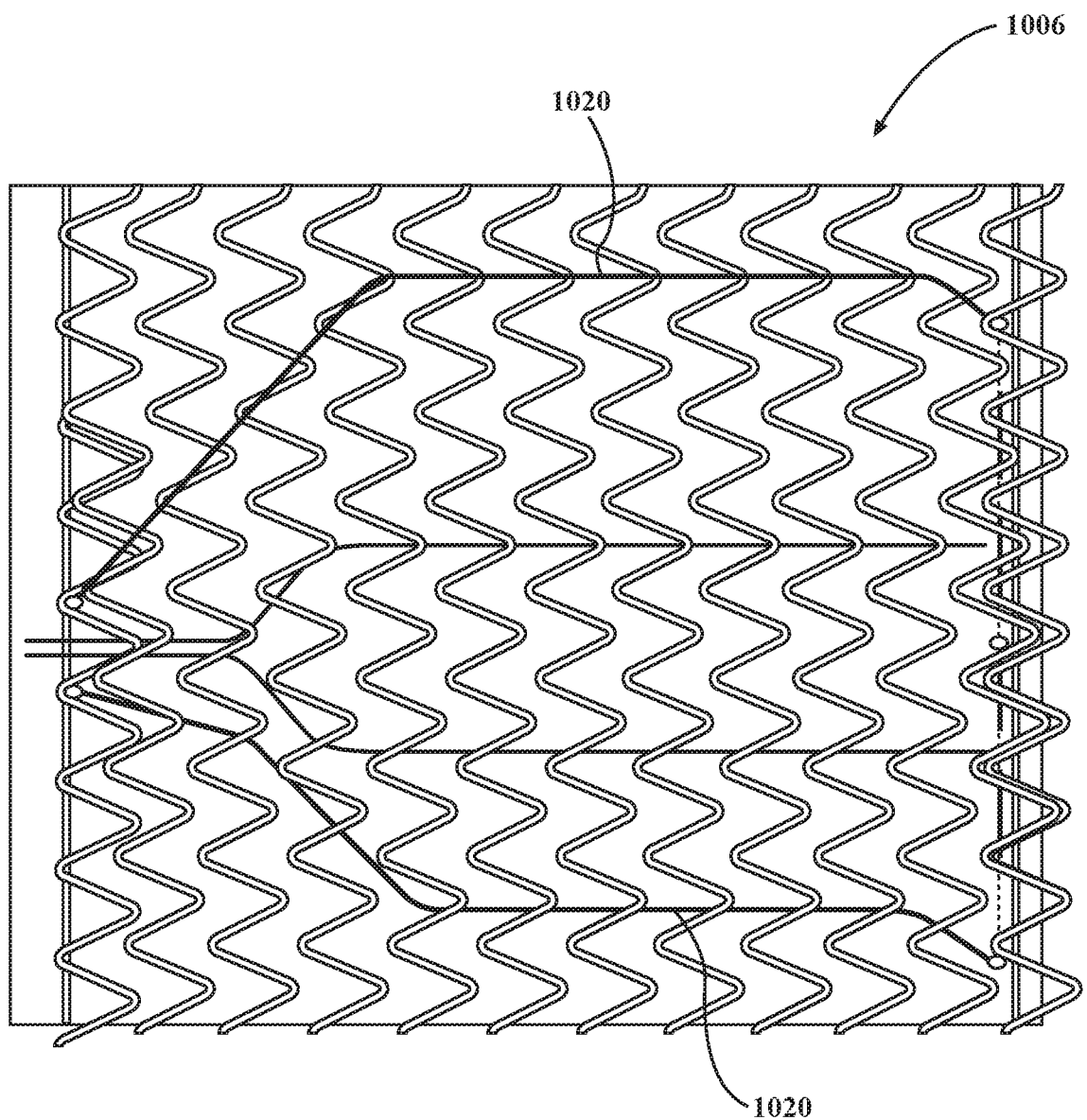

As illustrated in FIGS. 10B-10D, which illustrate inner curve, outer curve, and open views respectively of the expandable implant and steering lines illustrated in FIG. 10A, the helical pattern of each steering line 1020 begins near the distal end on the outer curve of expandable implant 1006 and terminates proximal thereto on the inner curve of expandable implant 1006. Each steering line 1020 continues in a direction substantially parallel to the central axis of expandable implant 1006 toward the proximal end on the inner curve of expandable implant 1006, where it circumferentially traverses expandable implant 1006 back to its outer curve. As illustrated in FIGS. 10B-10D, the pattern of each steering line 1020 mirrors the other across a sagittal plane through the central axis of expandable implant 1006. In this manner, steering lines 1020 cooperate to enable selective and controllable bending of expandable implant 1006, and also to enable non-concentric, temporary engagement of expandable implant 1006 in relation to catheter shaft 1002. Any configuration of steering lines 1020 and surface of expandable implant 1006 which allows for selective and controllable bending and non-concentric, temporary engagement of expandable implant 1006 is within the scope of the present disclosure.

Figure 11A:
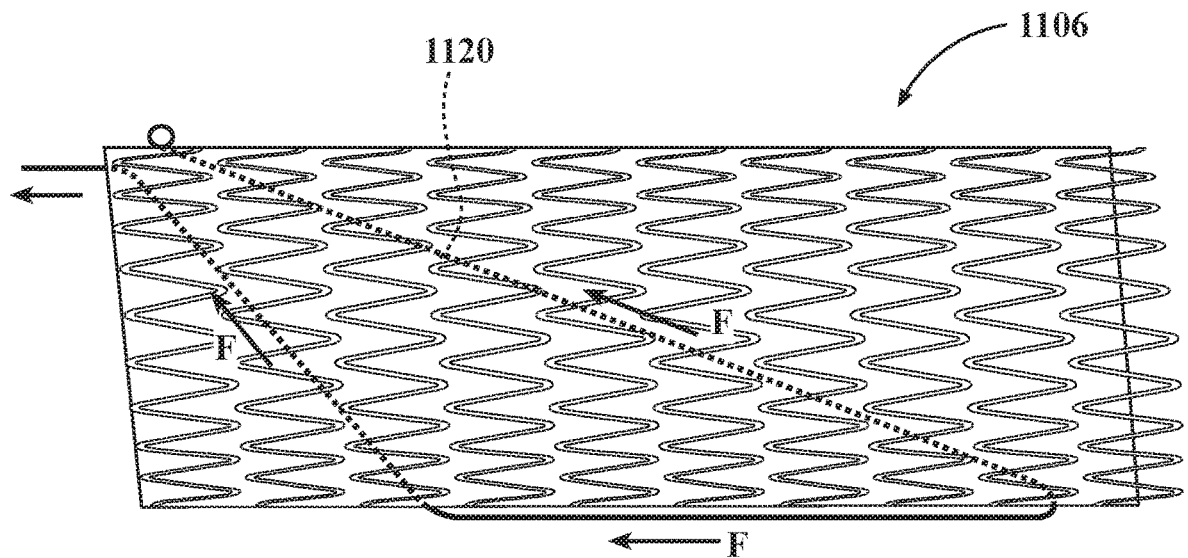
FIGS. 11A-11B illustrate additional embodiments of expandable implants having steering lines.
Figure 11B:
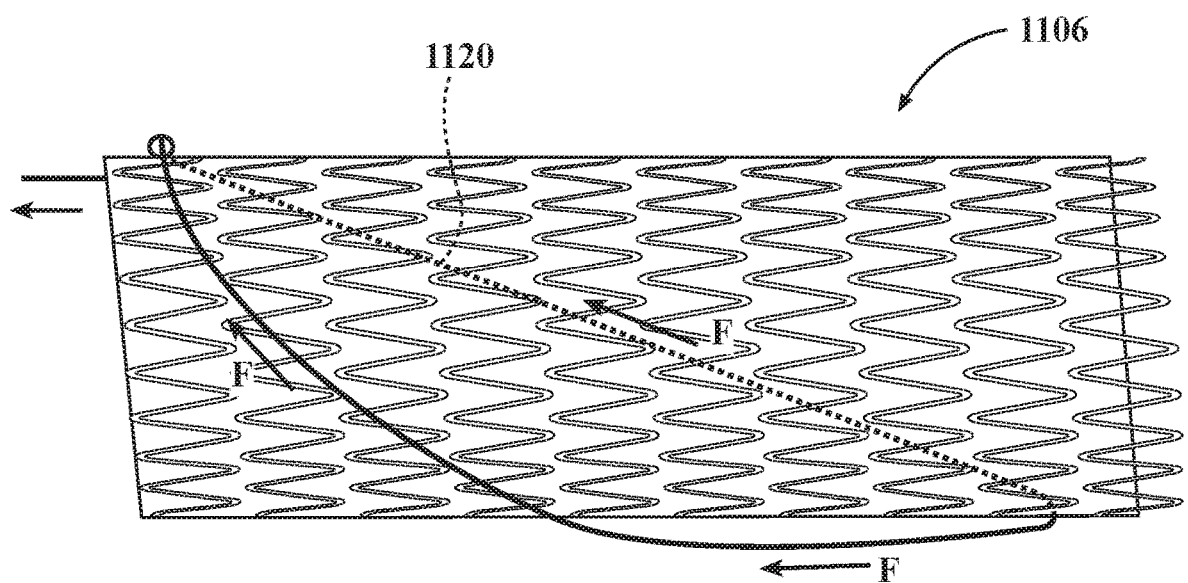

For example, and as illustrated in FIG. 11A, the helical pattern of the steering line 1120 begins on the exterior of expandable implant 1106 near the distal end on the outer curve of expandable implant 1106 and terminates proximal thereto on the inner curve of expandable implant 1106. The steering line 1120 continues on the inner curve in a direction substantially parallel to the central axis of expandable implant 1106 and toward the proximal end on the inner curve of expandable implant 1106. From the proximal end, the steering line 1120 enters expandable implant 1106 and returns to the distal end at the outer curve of expandable implant 1106, where it is locked with a distal pin. FIG. 11B illustrates a similar configuration, where like tensile forces F are applied to the steering line 1120, but where the steering line 1120 is threaded and locked in an opposite configuration.

In various embodiments, steering lines may traverse a path across and/or through the surface of expandable implant that is at least partially parallel to and substantially covered by one or more sleeves.

Figure 8:
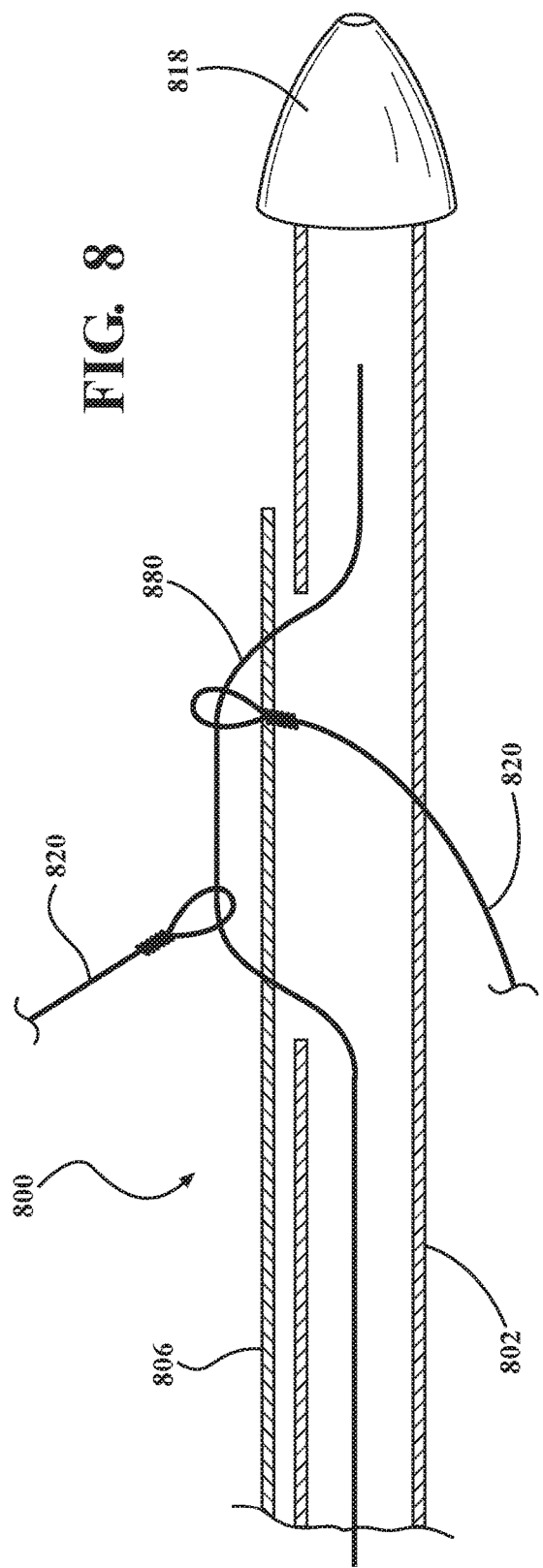
FIG. 8 illustrates a cross-sectional view of catheter assembly having an expandable implant.

In various embodiments, the catheter assembly may further comprise a lock wire. In such embodiments, the lock wire may secure a steering line or lines to the catheter assembly. For example, with reference to FIG. 8, catheter assembly 800 comprises a catheter shaft 802, expandable implant 806, two steering lines 820, and a lock wire 880. Lock wire 880 passes from outside of the body of the patient, through catheter shaft 802, and exits at a point near catheter tip 818. At this point, it interacts with steering lines 820, then reenters catheter shaft 802 and continues to catheter tip 818. In such a configuration, lock wire 880 releasably couples steering lines 820 to catheter assembly 800. Any manner in which lock wire 880 may interact with steering line or lines 820 to maintain a releasable coupling between steering line or lines 820 and catheter assembly 800 is within the scope of the present disclosure.

In various embodiments, each steering line may further comprise an end loop. For example, with reference to FIG. 9, each steering line 920 comprises an end loop 922. Lock wire 980 may pass through each end loop 922, securing each steering line 920 to catheter assembly 900. Any method of securing steering line or lines 920 to catheter assembly 900 is within the scope of the invention.

In various embodiments, lock wires can be formed from metallic, polymeric or natural materials and can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as stainless steels, cobalt-chromium alloys and nitinol. Elongated members or lock wires can also be formed from high strength polymer fibers such as ultra high molecular weight polyethylene fibers (e.g., Spectra®, Dyneema Purity®, etc.) or aramid fibers (e.g., Technora®, etc.).

In various embodiments, a catheter assembly used to deliver an expandable implant comprises a catheter shaft, an expandable implant, one or more sleeves, one or more steering lines, and a lock wire. In such configurations, the expandable implant is capable of bending, through tension applied to the one or more steering lines and corresponding displacement, to conform to curvature in the vasculature of a patient.

For example, with reference to FIGS. 5A-D, a catheter assembly 500 comprising an expandable implant 506 is illustrated. Catheter assembly 500 further comprises two steering lines 520, a lock wire 580, a primary coupling member 524, and a secondary coupling member 534. Primary coupling member 524 is releasably coupled to primary sleeve 504. Secondary coupling member 534 is releasably coupled to secondary sleeve 508.

Catheter assembly 500 is inserted into the vasculature of a patient, and expandable implant 506 is advanced to a treatment area of the vasculature. Upon arriving at a location close to the treatment area, primary coupling member 524 can be disengaged from primary sleeve 504, allowing expandable implant 506 to be expanded to an intermediate configuration. In various embodiments, sleeve 504 can be removed from the vasculature once primary coupling member 524 has been disengaged.

Figure 5B:
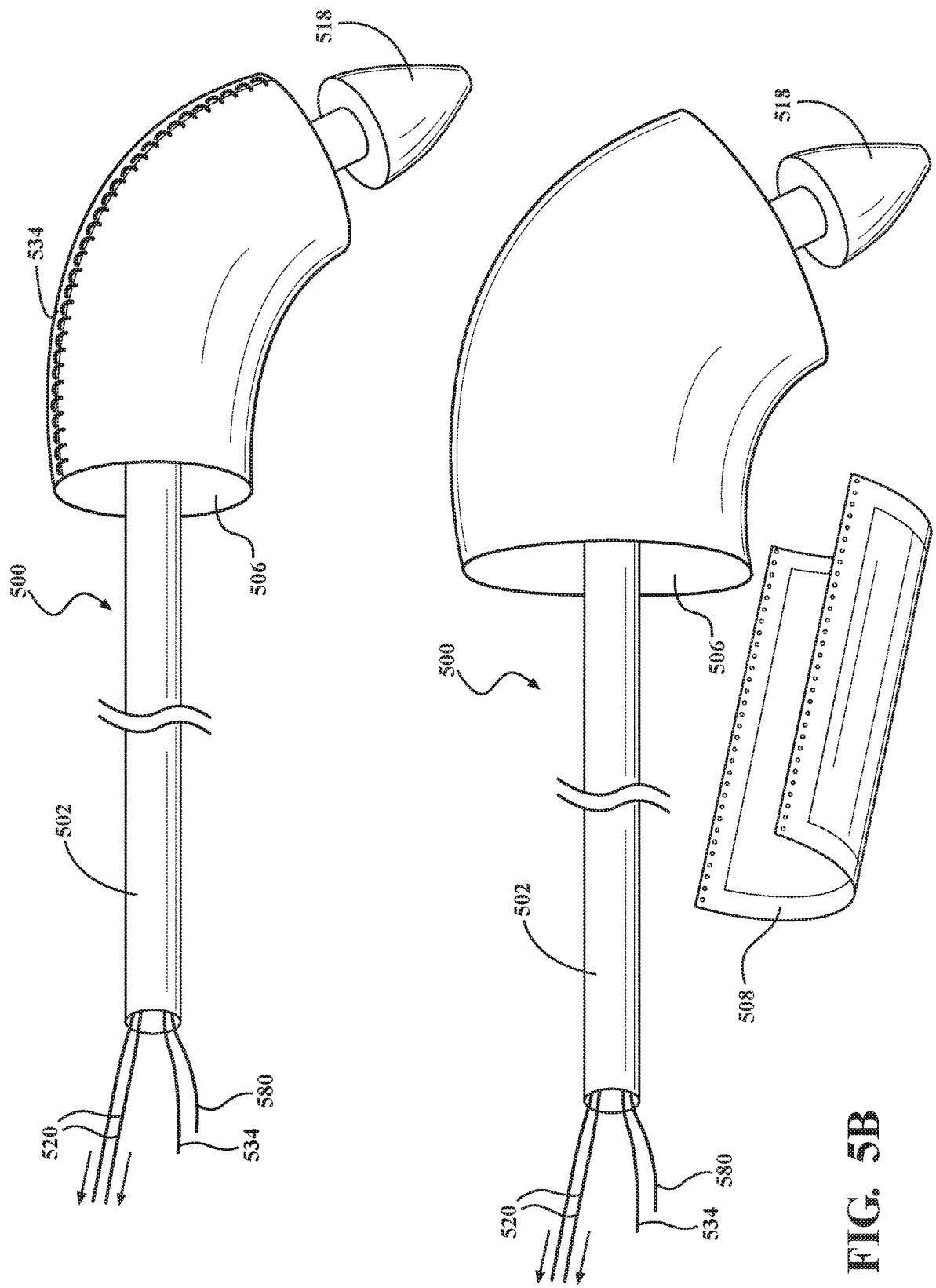

With reference to FIG. 5B, upon expansion to an intermediate configuration, tension can be applied to steering lines 520, causing expandable implant 506 to bend in a desired manner. For example, expandable implant 506 can bend in a direction aligned with the location of steering lines 520. Once expandable implant 506 has been sufficiently bent, consistent tension is applied to steering lines 520 to maintain the degree of bending.

In various embodiments, tension can be applied to steering lines 520 by pulling the lines from the outside of the body of the patient. In other embodiments, steering lines 520 can be connected to one or more dials or other mechanisms for applying the tension at the trailing end of catheter shaft 502. In this configuration, the dial can be used to apply a desired tension, as well as maintain the correct amount of tension once a desired angle of bending of expandable implant 506 has been achieved. Various embodiments may also comprise an indicator, scale, gradient, or the like which demonstrates the amount of tension or displacement of the steering line, and/or the amount of bending in expandable implant 506. In various embodiments, the catheter assembly can comprise one more additional markings (e.g., on a handle) that allow a user to determine the orientation of the steering line with respect to the vasculature.

After a sufficient degree of bending has been achieved in expandable implant 506, the implant can be rotated for final positioning in the treatment area of the vasculature. In various exemplary embodiments, lock wire 580 is engaged with steering lines 520 such that torsional rotation of the catheter shaft causes expandable implant 506 to rotate within the vasculature. However, any configuration of catheter assembly 500 which allows for rotation of expandable implant 506 is within the scope of the present disclosure.

In various embodiments, an expandable implant may further comprise one or more radiopaque markers. In one embodiment, one or more radiopaque markers form a band around the distal end of the expandable implant. In such configurations, the radiopaque markers may assist in deployment of an expandable implant by providing increased visibility when observing the expandable implant with a radiographic device, such as an x-ray machine. Any arrangement of radiopaque markers which assists in deployment of an expandable implant is within the scope of the present disclosure.

Figures 4A, 4B, 4C, 4D:
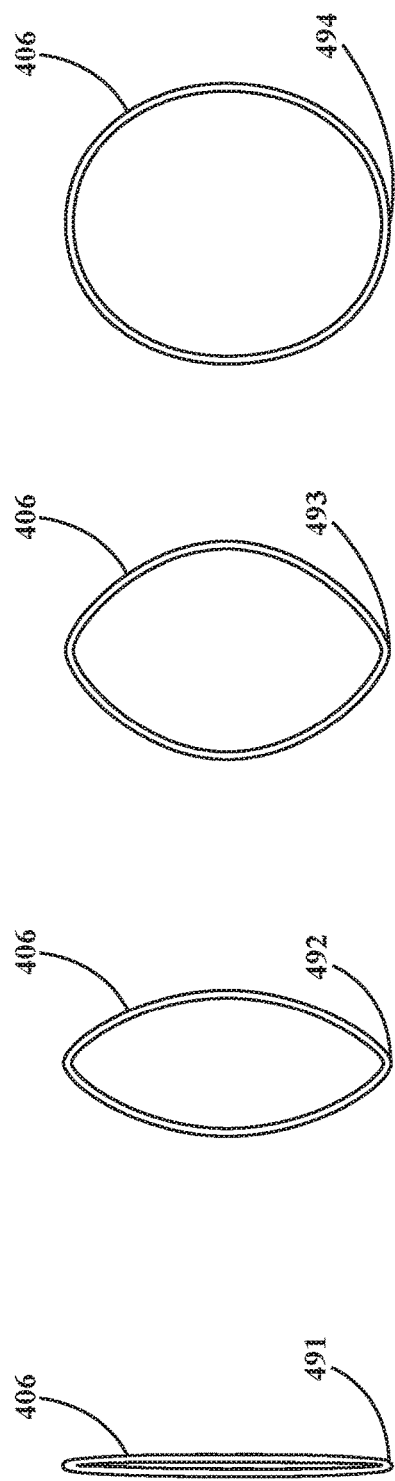
FIG. 4A-4D illustrates various profile views of a distal end of an expandable implant.
Figure 3A:
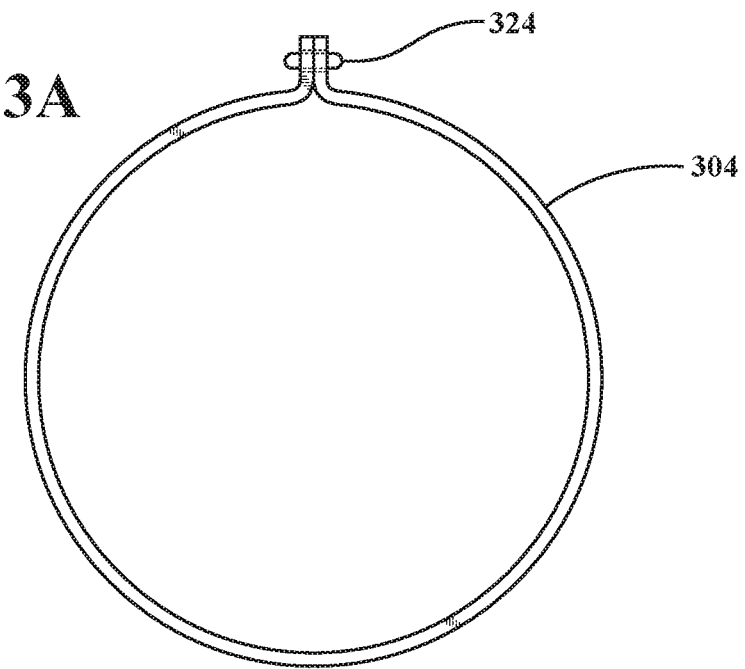
FIGS. 3A-3B and 3C-3D illustrate cross-sectional and perspective views, respectively, of catheter assemblies having expandable implants.
Figure 3B:
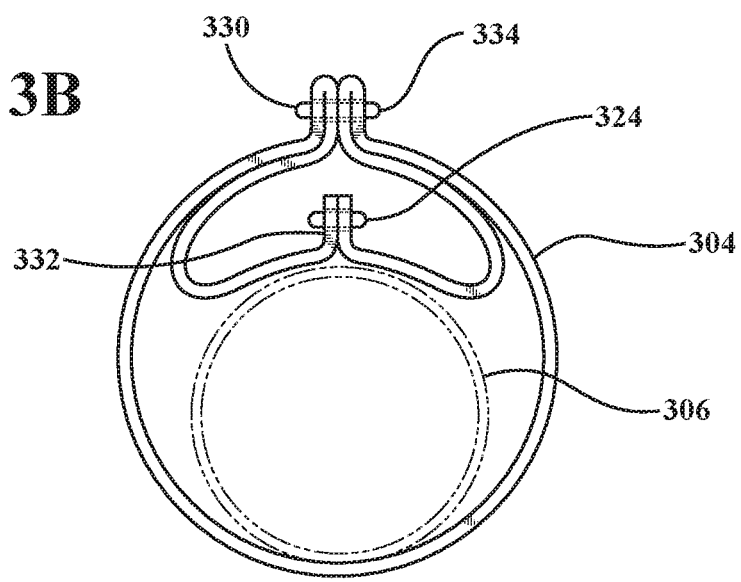
Figure 3C:
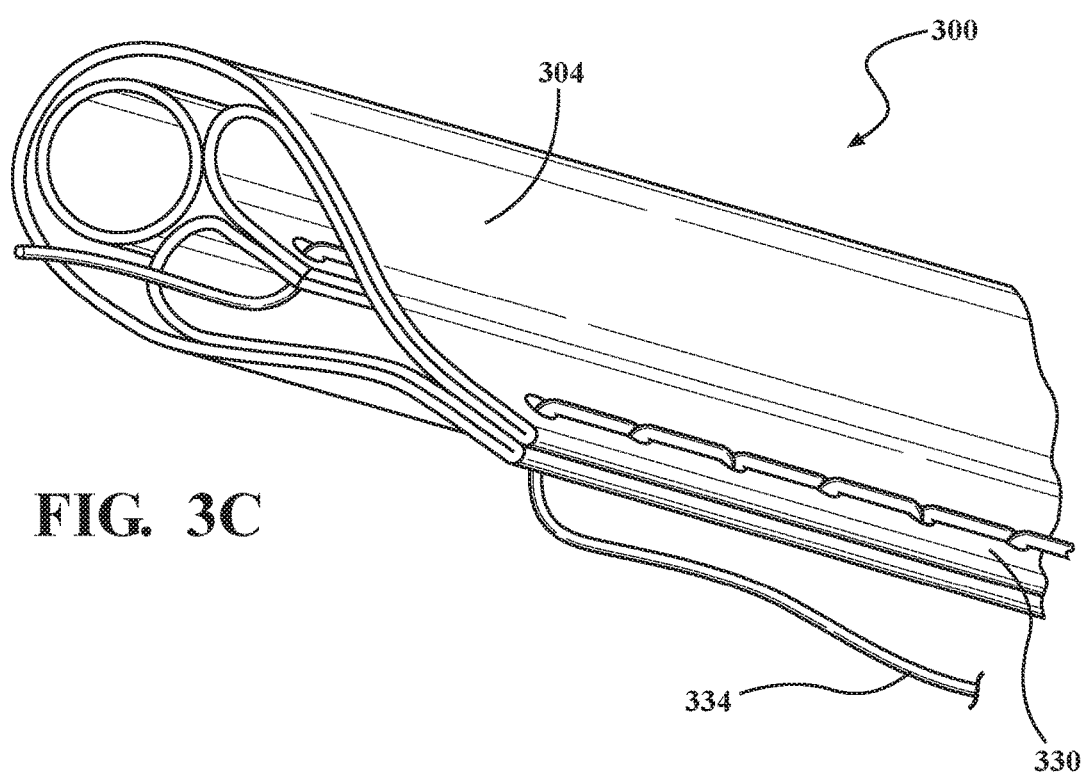
Figure 3D:
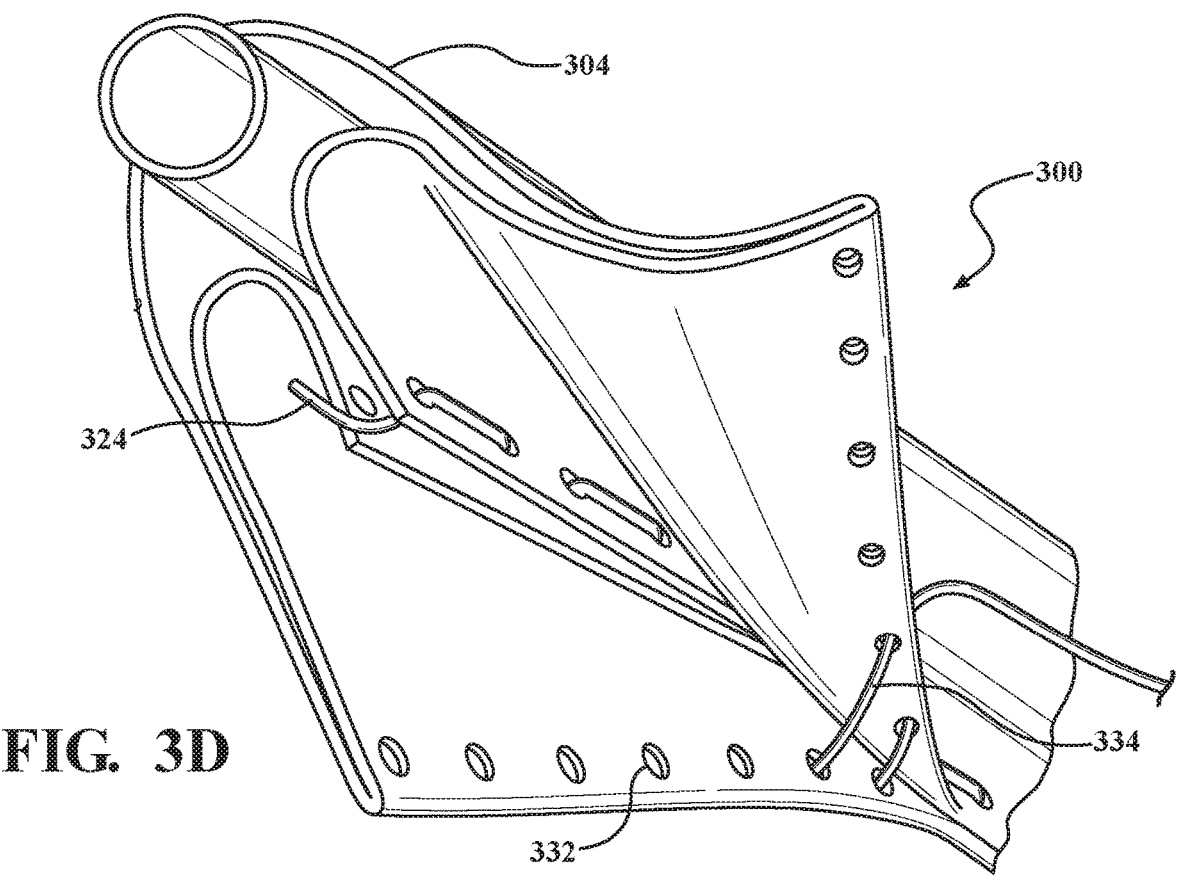

In various embodiments, radiopaque markers may assist in orienting the expandable implant by providing a profile view of the distal end of the expandable implant. For example, with reference to FIG. 4, a number of potential profiles 491-495 of the distal end of an expandable implant 406 are illustrated. In such configurations, radiopaque markers located in the distal end of expandable implant 406 provide a profile view of the distal end of expandable implant 406 when viewed by a radiographic device. Such profile views can be used to properly orient expandable implant 406 by assisting a user in determining the degree of rotation and/or orientation of a bend in expandable implant 406.

For example, profile 491 represents a distal end of an expandable implant 406 having an orientation substantially orthogonal to a radiographic image capture device, such as an x-ray camera. Profile 492 represents a distal end of an expandable implant having an orientation less orthogonal than profile 491. Profile 493 represents a distal end of an expandable implant 406 having an orientation less orthogonal than profile 492. Finally, profile 494 represents a distal end of an expandable implant 406 having an orientation parallel to a radiographic image capture device.

After expandable implant 506 has been properly oriented and located within the treatment area of the patient, secondary coupling member 534 can be disengaged from secondary sleeve 508. Once secondary coupling member 534 is disengaged from secondary sleeve 508, expandable implant 506 can be expanded to a final position and diameter within the treatment area. In various exemplary embodiments, secondary sleeve 508 is removed from the vasculature. In other exemplary embodiments, secondary sleeve 508 remains in position circumferentially surrounding a portion of expandable implant 506.

Figure 5C:
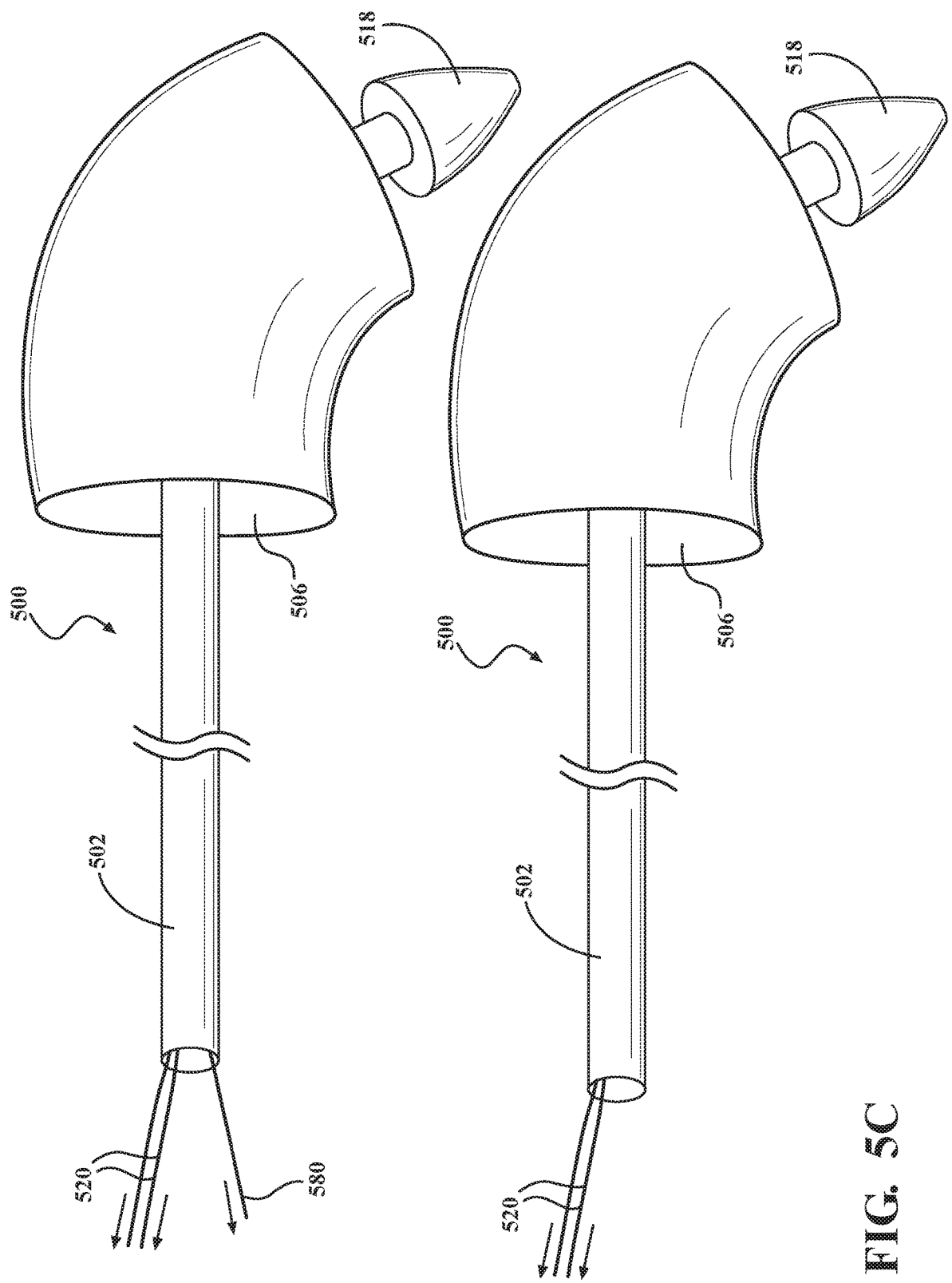

With reference to FIG. 5C, after expandable implant 506 is in position and expanded within the vasculature, lock wire 580 can be disengaged from catheter assembly 500. In various embodiments, lock wire 580 is disengaged by applying sufficient tension to the lock wire 580 from outside of the body of the patient. After lock wire 580 is disengaged, steering lines 520 can be released from coupling with catheter shaft 502 and can be removed from expandable implant 506 and catheter assembly 500.

Figure 5D:
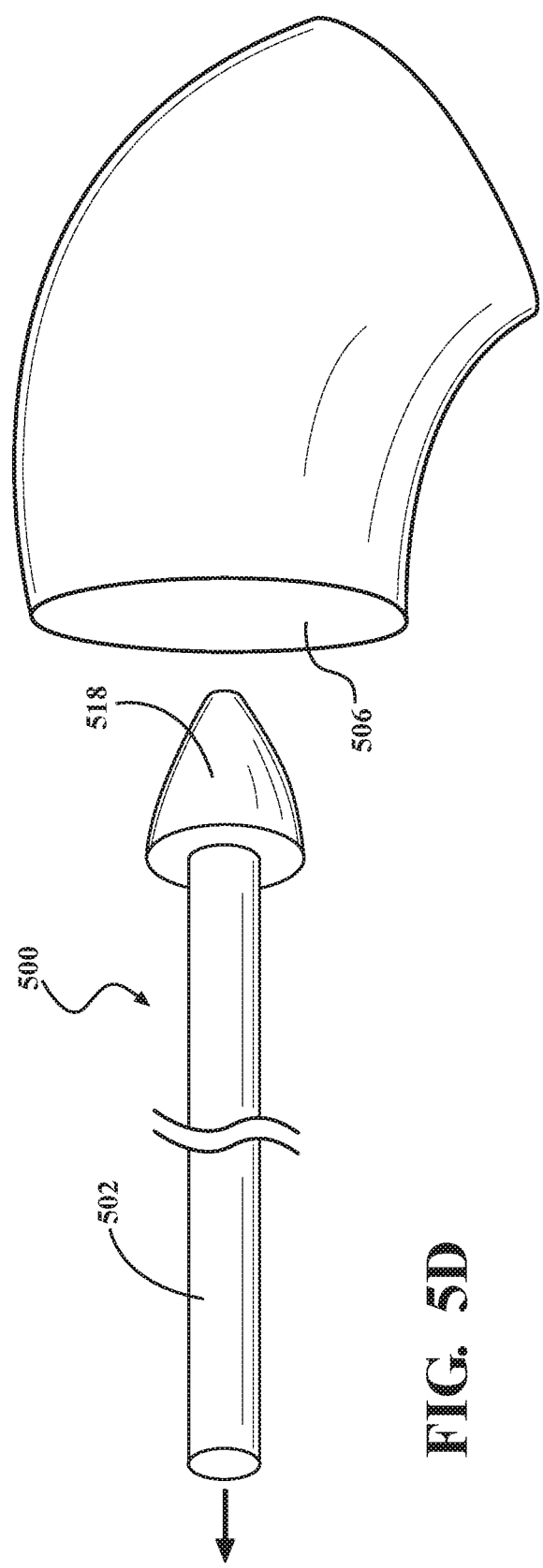

As illustrated in FIG. 5D, after primary and secondary coupling members 524 and 534, steering lines 520, and lock wire 580 are removed from catheter assembly 500, catheter assembly 500 is fully disengaged from expandable implant 506, and can be removed from the vasculature of the patient.

It will be apparent to those skilled in the art that various modifications and variations can be made in the present disclosure without departing from the spirit or scope of the disclosure. Thus, it is intended that the present disclosure cover the modifications and variations of this disclosure provided they come within the scope of the appended claims and their equivalents.

Likewise, numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed is:

1. A catheter assembly comprising:
a catheter shaft having a leading end and a trailing end and comprising a main lumen extending between the leading end and the trailing end;
an expandable medical device positioned at the leading end of the catheter shaft; and
steering lines configured to selectively bend the expandable medical device, each steering line begins near a distal end on an outer curve of the expandable medical device and terminates proximal thereto on an inner curve of the expandable medical device with each steering line continuing in a direction substantially parallel to a central axis of the expandable medical device toward a proximal end on the inner curve of the expandable medical device where each steering line circumferentially traverses the expandable medical device back to the outer curve.

2. The catheter assembly of claim 1, wherein the steering lines enable non-concentric, temporary engagement of the expandable medical device in relation to the catheter.

3. The catheter assembly of claim 1, wherein the steering lines comprise at least one of nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, and elastomeric organosilicon polymers.

4. The catheter assembly of claim 1, wherein the expandable medical device is configured to radially collapse into a collapsed configuration suitable for delivery, and expand to a radially expanded configuration when unrestrained.

5. The catheter assembly of claim 1, further comprising a handle coupled to the catheter shaft, and the handle comprises one or more mechanisms configured to apply tension to the steering lines to selectively bend the expandable medical device.

6. The catheter assembly of claim 1, further comprising a lock wire configured to releasably couple the steering lines to the expandable medical device.

7. A catheter assembly comprising:
a catheter shaft having a leading end and a trailing end and comprising a main lumen extending between the leading end and the trailing end;
an expandable medical device positioned at the leading end of the catheter shaft; steering lines configured to selectively bend the expandable medical device, each steering line begins near a distal end on an outer curve of the expandable medical device and terminates proximal thereto on an inner curve of the expandable medical device implant with each steering line continuing in a direction substantially parallel to a central axis of the expandable medical device toward a proximal end on the inner curve of the expandable medical device where each steering line circumferentially traverses the expandable medical device back to the outer curve; and
a lock wire configured to releasably couple the steering lines to the expandable medical device.

8. The catheter assembly of claim 7, wherein the lock wire is configured to releasably couple the steering lines to the catheter shaft.

9. The catheter assembly of claim 7, further comprising a catheter tip arranged at the leading end of the catheter shaft, and wherein the lock wire engages the steering lines and continues to the catheter tip.

10. The catheter assembly of claim 7, wherein the steering lines are woven through the expandable medical device.

11. The catheter assembly of claim 7, wherein the lock wire engages with the steering lines and torsionally anchors the expandable medical device and the catheter shaft allowing rotational positioning of the expandable medical device at a treatment site via rotation of the catheter shaft.

12. The catheter assembly of claim 7, further comprising a constraint mechanism to allow partial deployment of the expandable medical device toward an intermediate configuration sized between a delivery configuration and a fully deployed configuration.

13. A method of deploying an expandable medical device, the method comprising:
arranging a catheter shaft carrying the expandable medical device at a treatment location, the catheter shaft having a leading end and a trailing end and comprising a main lumen extending between the leading end and the trailing end;

actuating steering lines to selectively bend the expandable medical device, each steering line begins near a distal end on an outer curve of the expandable medical device and terminates proximal thereto on an inner curve of the expandable medical device with each steering line continuing in a direction substantially parallel to a central axis of the expandable medical device toward a proximal end on the inner curve of the expandable medical device where each steering line circumferentially traverses the expandable medical device back to the outer curve; and deploying the expandable medical device at the treatment site.

14. The method of claim 13, wherein deploying the expandable medical device comprises releasing a lock wire, releasably coupling to the steering lines to the expandable medical device, to deploy the expandable medical device at the treatment site.

15. The method of claim 13, wherein further comprising releasing a constraint mechanism to allow partial deployment of the expandable medical device toward an intermediate configuration sized between a delivery configuration and a fully deployed configuration.

16. The method of claim 15, wherein deploying the expandable medical device comprises deploying the expandable medical device from the intermediate configuration to the fully deployed configuration.

\* \* \* \* \*